United States Patent
Xi et al.

(10) Patent No.: US 9,476,093 B2
(45) Date of Patent: Oct. 25, 2016

(54) POLYMERIZATION OF NUCLEIC ACIDS USING ACTIVATION BY POLYPHOSPHOROLYSIS (APP) REACTIONS

(71) Applicant: LIFE TECHNOLOGIES CORPORATION, Carlsbad, CA (US)

(72) Inventors: Lei Xi, Foster City, CA (US); Paul Kenney, Sunnyvale, CA (US); Zhaochun Ma, Sunnyvale, CA (US); Dennis Prosen, Foster City, CA (US); Stephen Hendricks, Los Gatos, CA (US); Roland Nagel, Santa Cruz, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/593,858

(22) Filed: Jan. 9, 2015

(65) Prior Publication Data
US 2015/0191775 A1    Jul. 9, 2015

Related U.S. Application Data

(62) Division of application No. 13/324,676, filed on Dec. 13, 2011, now Pat. No. 8,932,813.

(60) Provisional application No. 61/422,477, filed on Dec. 13, 2010.

(51) Int. Cl.
| | |
|---|---|
| *C12Q 1/68* | (2006.01) |
| *C12P 19/34* | (2006.01) |
| *C07H 21/00* | (2006.01) |
| *C12N 15/10* | (2006.01) |

(52) U.S. Cl.
CPC ............... *C12Q 1/686* (2013.01); *C07H 21/00* (2013.01); *C12N 15/10* (2013.01); *C12Q 1/6869* (2013.01)

(58) Field of Classification Search
CPC .............................. C12Q 1/686; C12Q 1/6869
USPC .................................................... 435/6.1, 91.1
See application file for complete search history.

(56) References Cited

U.S. PATENT DOCUMENTS

| | | | |
|---|---|---|---|
| 4,683,202 | A | 7/1987 | Mullis |
| 4,889,818 | A | 12/1989 | Gelfand et al. |
| 5,047,342 | A | 9/1991 | Chatterjee |
| 5,079,352 | A | 1/1992 | Gelfand et al. |
| 5,270,179 | A | 12/1993 | Chatterjee |
| 5,374,553 | A | 12/1994 | Gelfand et al. |
| 5,436,149 | A | 7/1995 | Barnes |
| 5,512,462 | A | 4/1996 | Cheng |
| 5,602,000 | A | 2/1997 | Hyman |

(Continued)

FOREIGN PATENT DOCUMENTS

| | | |
|---|---|---|
| WO | WO-03/095664 | 11/2003 |
| WO | WO-2012/082753 | 6/2012 |

OTHER PUBLICATIONS 11848096.1, "European Search Report mailed May 27, 2014", 3 pgs.

(Continued)

*Primary Examiner* — Jezia Riley

(57) ABSTRACT

This disclosure relates to methods of performing activation by polyphosphorolysis (APP) reactions using at least one of the polyphosphorylating agents triphosphate, polyphosphate, imidodiphosphate, thiodiphosphate (or μ-monothiopyrophosphate), and related compounds.

17 Claims, 30 Drawing Sheets

(56) References Cited

U.S. PATENT DOCUMENTS

| | | | |
|---|---|---|---|
| 5,614,365 | A | 3/1997 | Tabor et al. |
| 6,228,628 | B1 | 5/2001 | Gelfand et al. |
| 6,534,269 | B2 | 3/2003 | Liu et al. |
| 7,033,763 | B2 | 4/2006 | Liu et al. |
| 7,105,298 | B2 | 9/2006 | Liu et al. |
| 7,211,414 | B2 | 5/2007 | Hardin et |
| 7,238,480 | B2 | 7/2007 | Liu et al. |
| 7,422,872 | B2 | 9/2008 | Rozzelle et al. |
| 7,504,221 | B2 | 3/2009 | Liu et al. |
| 7,745,125 | B2 | 6/2010 | Gelfand et al. |
| 7,794,984 | B2 | 9/2010 | Kless |
| 7,919,253 | B2 | 4/2011 | Liu et al. |
| 8,314,216 | B2 * | 11/2012 | Hardin .................. C07H 19/06 435/6.12 |
| 2004/0009515 | A1 | 1/2004 | Liu et al. |
| 2005/0037398 | A1 | 2/2005 | Gelfand et al. |
| 2007/0020622 | A1 | 1/2007 | Lee et al. |
| 2007/0154914 | A1 | 7/2007 | Gelfand et al. |
| 2007/0299249 | A1 | 12/2007 | Songe |
| 2008/0254525 | A1 | 10/2008 | Zheng et al. |
| 2009/0155802 | A1 | 6/2009 | Bauer et al. |

OTHER PUBLICATIONS

Deutscher, et al., "Enzymatic Synthesis of Deoxyribonucleic Acid: XXVIII. The Pyrophosphate Exchange and Pyrophosphorolysis Reactions of Deoxyribonucleic Acid Polymerase", *The Journal of Biological Chemistry*, vol. 244, No. 11, USA, Jun. 10, 1996, 3019-3028.

Liu, et al., "Pyrophosphorolysis-activatable oligonucleotides may facilitate detection of rare alleles, mutation scanning and analysis of chromatin structures", *Nucleic Acids Research, Oxford University Press*, vol. 30, No. 2, Jan. 15, 2002, 598-604.

Liu, et al., "Pyrophosphorolysis-Activated Polymerization (PAP): Application to Allele-Specific Amplification", *BioTechniques* 29(5), Nov. 1, 2000, 1072-1083.

PCT/US2011/064668, "International Search Report mailed Aug. 31, 2012", 6 Pgs.

Wu, J et al., "Termination of DNA synthesis by N6-alkylated, not 3'-O-alkylated, photocleavable 2'—deoxyadenosine triphosphates", *Nuc Acids Research*, vol. 35(19), 2007, pp. 6339-6349.

\* cited by examiner

Amplification of a plasmid template by Power SYBR

Triphosphate-catalyzed APP amplification from plasmid DNA

Lane 8C1    Lane 8C2

Amplification curves and melting curves of triphosphate-and PPi-reactions

Amplification curves and melting curves of triphosphate-and PPi-reactions

Relative rates of linear amplifications of three reactions using perfectly matched substrates and mismatches substrates

|  | Regular PCR | TP-reaction | PPi-reaction |
|---|---|---|---|
| Perfectly Matched Template | 100% | 100% | 100% |
| Mismatched @ -1 | 28% | 0.46% | 0.98% |

Ethidium Bromide agarose gel, under UV light

IDP

SEQUENCE LISTING

<160> NUMBER OF SEQ ID NOS: 69

<210> SEQ ID NO 1
<211> LENGTH: 25
<212> TYPE: DNA
<213> ORGANISM: Artificial sequence
<220> FEATURE:
<223> OTHER INFORMATION: Primer sequence

<400> SEQUENCE: 1
catcctggtt tgtgttttgc ctaac                                                25

<210> SEQ ID NO 2
<211> LENGTH: 25
<212> TYPE: DNA
<213> ORGANISM: Artificial sequence
<220> FEATURE:
<223> OTHER INFORMATION: Primer sequence

<400> SEQUENCE: 2
gggagaaaaa agccaacctt aatgc                                                25

<210> SEQ ID NO 3
<211> LENGTH: 21
<212> TYPE: DNA
<213> ORGANISM: Artificial sequence
<220> FEATURE:
<223> OTHER INFORMATION: Primer sequence

<400> SEQUENCE: 3
tgcaataccg tgagctgacc c                                                    21

<210> SEQ ID NO 4
<211> LENGTH: 25
<212> TYPE: DNA
<213> ORGANISM: Artificial sequence
<220> FEATURE:
<223> OTHER INFORMATION: Primer sequence

<400> SEQUENCE: 4
gtctggttga aacgagtgtg caggc                                                25

<210> SEQ ID NO 5
<211> LENGTH: 103
<212> TYPE: DNA
<213> ORGANISM: Artificial sequence
<220> FEATURE:
<223> OTHER INFORMATION: Primer sequence

<400> SEQUENCE: 5
tgcaataccg tgagctgacc cgtctgcgtt cgacctacat cgacccactg ccggacctga         60
ttcatccacg taccggccgc ctgcacactc gtttcaacca gac                          103

<210> SEQ ID NO 6
<211> LENGTH: 23
<212> TYPE: DNA
<213> ORGANISM: Artificial sequence
<220> FEATURE:
<223> OTHER INFORMATION: Primer sequence

<400> SEQUENCE: 6
gcatagcagt ccccaagaat gac                                                  23

<210> SEQ ID NO 7
<211> LENGTH: 21

<212> TYPE: DNA
<213> ORGANISM: Artificial sequence
<220> FEATURE:
<223> OTHER INFORMATION: Primer sequence

<400> SEQUENCE: 7
cggttcccac gaaaagcaac c                                          21

<210> SEQ ID NO 8
<211> LENGTH: 22
<212> TYPE: DNA
<213> ORGANISM: Artificial sequence
<220> FEATURE:
<223> OTHER INFORMATION: Primer sequence

<400> SEQUENCE: 8
gctccagaca gaaacaccgt ac                                         22

<210> SEQ ID NO 9
<211> LENGTH: 24
<212> TYPE: DNA
<213> ORGANISM: Artificial sequence
<220> FEATURE:
<223> OTHER INFORMATION: Primer sequence

<400> SEQUENCE: 9
ccataaccag actcagcaga gaac                                       24

<210> SEQ ID NO 10
<211> LENGTH: 46
<212> TYPE: DNA
<213> ORGANISM: Artificial sequence
<220> FEATURE:
<223> OTHER INFORMATION: Primer sequence

<400> SEQUENCE: 10
cagcgtgtgg tatgcgtcga cgttaggcaa aacacaaacc aggatg               46

<210> SEQ ID NO 11
<211> LENGTH: 25
<212> TYPE: DNA
<213> ORGANISM: Artificial sequence
<220> FEATURE:
<223> OTHER INFORMATION: Primer sequence

<400> SEQUENCE: 11
catcctggtt tgtgttttgc ctaat                                      25

<210> SEQ ID NO 12
<211> LENGTH: 46
<212> TYPE: DNA
<213> ORGANISM: Artificial sequence
<220> FEATURE:
<223> OTHER INFORMATION: Primer sequence

<400> SEQUENCE: 12
cagcgtgtgg tatgcgtcga ctttaggcaa aacacaaacc aggatg               46

<210> SEQ ID NO 13
<211> LENGTH: 23
<212> TYPE: DNA
<213> ORGANISM: Artificial sequence
<220> FEATURE:
<223> OTHER INFORMATION: Primer sequence

<400> SEQUENCE: 13
gatcctttag tgctggactg acc                                    23

<210> SEQ ID NO 14
<211> LENGTH: 44
<212> TYPE: DNA
<213> ORGANISM: Artificial sequence
<220> FEATURE:
<223> OTHER INFORMATION: Primer sequence

<400> SEQUENCE: 14
cagcgtgtgg tatgcgtcga cggtcagtcc agcactaaag gatc              44

<210> SEQ ID NO 15
<211> LENGTH: 21
<212> TYPE: DNA
<213> ORGANISM: Artificial sequence
<220> FEATURE:
<223> OTHER INFORMATION: Primer sequence

<400> SEQUENCE: 15
tgcaataccg tgagctgacc c                                       21

<210> SEQ ID NO 16
<211> LENGTH: 24
<212> TYPE: DNA
<213> ORGANISM: Artificial sequence
<220> FEATURE:
<223> OTHER INFORMATION: Primer sequence

<400> SEQUENCE: 16
ccataaccag actcagcaga gaac                                    24

<210> SEQ ID NO 17
<211> LENGTH: 22
<212> TYPE: DNA
<213> ORGANISM: Artificial sequence
<220> FEATURE:
<223> OTHER INFORMATION: Primer sequence

<400> SEQUENCE: 17
gctccagaca gaaacaccgt tc                                      22

<210> SEQ ID NO 18
<211> LENGTH: 22
<212> TYPE: DNA
<213> ORGANISM: Artificial sequence
<220> FEATURE:
<223> OTHER INFORMATION: Primer sequence

<400> SEQUENCE: 18
gctccagaca gaaacagttc tc                                      22

<210> SEQ ID NO 19
<211> LENGTH: 22
<212> TYPE: DNA
<213> ORGANISM: Artificial sequence
<220> FEATURE:
<223> OTHER INFORMATION: Primer sequence

<400> SEQUENCE: 19
gctccagaca gaagttctct gc                                      22

<210> SEQ ID NO 20
<211> LENGTH: 25
<212> TYPE: DNA
<213> ORGANISM: Artificial sequence

```
<220> FEATURE:
<223> OTHER INFORMATION: Primer sequence

<400> SEQUENCE: 20
catcctggtt tgtgttttgc ctaac                                          25

<210> SEQ ID NO 21
<211> LENGTH: 27
<212> TYPE: DNA
<213> ORGANISM: Artificial sequence
<220> FEATURE:
<223> OTHER INFORMATION: Primer sequence

<400> SEQUENCE: 21
gacaatactg ttccaatttg gctcatc                                        27

<210> SEQ ID NO 22
<211> LENGTH: 25
<212> TYPE: DNA
<213> ORGANISM: Artificial sequence
<220> FEATURE:
<223> OTHER INFORMATION: Primer sequence

<400> SEQUENCE: 22
gctccagttg tatcatcccc ttttc                                          25

<210> SEQ ID NO 23
<211> LENGTH: 27
<212> TYPE: DNA
<213> ORGANISM: Artificial sequence
<220> FEATURE:
<223> OTHER INFORMATION: Primer sequence

<400> SEQUENCE: 23
cacaaagaca cgaagaacat cattgac                                        27

<210> SEQ ID NO 24
<211> LENGTH: 25
<212> TYPE: DNA
<213> ORGANISM: Artificial sequence
<220> FEATURE:
<223> OTHER INFORMATION: Primer sequence

<400> SEQUENCE: 24
gggatggctc tatggacaaa aagac                                          25

<210> SEQ ID NO 25
<211> LENGTH: 25
<212> TYPE: DNA
<213> ORGANISM: Artificial sequence
<220> FEATURE:
<223> OTHER INFORMATION: Primer sequence

<400> SEQUENCE: 25
tgccatggtg cttcatacaa gtatc                                          25

<210> SEQ ID NO 26
<211> LENGTH: 28
<212> TYPE: DNA
<213> ORGANISM: Artificial sequence
<220> FEATURE:
<223> OTHER INFORMATION: Primer sequence

<400> SEQUENCE: 26
cccggttaaa taccatgaga ttctaagc                                       28
```

<210> SEQ ID NO 27
<211> LENGTH: 26
<212> TYPE: DNA
<213> ORGANISM: Artificial sequence
<220> FEATURE:
<223> OTHER INFORMATION: Primer sequence

<400> SEQUENCE: 27
ggagcaagct tgaaggagtt agaatc                                      26

<210> SEQ ID NO 28
<211> LENGTH: 25
<212> TYPE: DNA
<213> ORGANISM: Artificial sequence
<220> FEATURE:
<223> OTHER INFORMATION: Primer sequence

<400> SEQUENCE: 28
ccatcaggga agactatcct caaac                                       25

<210> SEQ ID NO 29
<211> LENGTH: 23
<212> TYPE: DNA
<213> ORGANISM: Artificial sequence
<220> FEATURE:
<223> OTHER INFORMATION: Primer sequence

<400> SEQUENCE: 29
gcatagcagt ccccaagaat gac                                         23

<210> SEQ ID NO 30
<211> LENGTH: 19
<212> TYPE: DNA
<213> ORGANISM: Artificial sequence
<220> FEATURE:
<223> OTHER INFORMATION: Primer sequence

<400> SEQUENCE: 30
ctcgccatcc ccaccatac                                              19

<210> SEQ ID NO 31
<211> LENGTH: 21
<212> TYPE: DNA
<213> ORGANISM: Artificial sequence
<220> FEATURE:
<223> OTHER INFORMATION: Primer sequence

<400> SEQUENCE: 31
cctcttcatc ctcacccttg c                                           21

<210> SEQ ID NO 32
<211> LENGTH: 22
<212> TYPE: DNA
<213> ORGANISM: Artificial sequence
<220> FEATURE:
<223> OTHER INFORMATION: Primer sequence

<400> SEQUENCE: 32
cctgcccttc agaacctaac ac                                          22

<210> SEQ ID NO 33
<211> LENGTH: 21
<212> TYPE: DNA
<213> ORGANISM: Artificial sequence
<220> FEATURE:
<223> OTHER INFORMATION: Primer sequence

<400> SEQUENCE: 33
tcagcacacc tatcggaaag c                                              21

<210> SEQ ID NO 34
<211> LENGTH: 17
<212> TYPE: DNA
<213> ORGANISM: Artificial sequence
<220> FEATURE:
<223> OTHER INFORMATION: Primer sequence

<400> SEQUENCE: 34
gcggatgcct cctttgc                                                   17

<210> SEQ ID NO 35
<211> LENGTH: 23
<212> TYPE: DNA
<213> ORGANISM: Artificial sequence
<220> FEATURE:
<223> OTHER INFORMATION: Primer sequence

<400> SEQUENCE: 35
gatcctttag tgctggactg acc                                            23

<210> SEQ ID NO 36
<211> LENGTH: 22
<212> TYPE: DNA
<213> ORGANISM: Artificial sequence
<220> FEATURE:
<223> OTHER INFORMATION: Primer sequence

<400> SEQUENCE: 36
gctccagaca gaaacaccgt ac                                             22

<210> SEQ ID NO 37
<211> LENGTH: 21
<212> TYPE: DNA
<213> ORGANISM: Artificial sequence
<220> FEATURE:
<223> OTHER INFORMATION: Primer sequence

<400> SEQUENCE: 37
atccttggtg ggactgaaca c                                              21

<210> SEQ ID NO 38
<211> LENGTH: 22
<212> TYPE: DNA
<213> ORGANISM: Artificial sequence
<220> FEATURE:
<223> OTHER INFORMATION: Primer sequence

<400> SEQUENCE: 38
cagagagcgc ctcctattct ac                                             22

<210> SEQ ID NO 39
<211> LENGTH: 22
<212> TYPE: DNA
<213> ORGANISM: Artificial sequence
<220> FEATURE:
<223> OTHER INFORMATION: Primer sequence

<400> SEQUENCE: 39
ggagagagac ctgggaaaag tc                                             22

<210> SEQ ID NO 40

```
<211> LENGTH: 23
<212> TYPE: DNA
<213> ORGANISM: Artificial sequence
<220> FEATURE:
<223> OTHER INFORMATION: Primer sequence

<400> SEQUENCE: 40
aagcgctatg cagagaagta ctc                                            23

<210> SEQ ID NO 41
<211> LENGTH: 21
<212> TYPE: DNA
<213> ORGANISM: Artificial sequence
<220> FEATURE:
<223> OTHER INFORMATION: Primer sequence

<400> SEQUENCE: 41
gacacgtgct tgaggaaaca c                                              21

<210> SEQ ID NO 42
<211> LENGTH: 22
<212> TYPE: DNA
<213> ORGANISM: Artificial sequence
<220> FEATURE:
<223> OTHER INFORMATION: Primer sequence

<400> SEQUENCE: 42
gcagactagg ctgcattcac tc                                             22

<210> SEQ ID NO 43
<211> LENGTH: 19
<212> TYPE: DNA
<213> ORGANISM: Artificial sequence
<220> FEATURE:
<223> OTHER INFORMATION: Primer sequence

<400> SEQUENCE: 43
agagctgcgt ggacactac                                                 19

<210> SEQ ID NO 44
<211> LENGTH: 25
<212> TYPE: DNA
<213> ORGANISM: Artificial sequence
<220> FEATURE:
<223> OTHER INFORMATION: Primer sequence

<400> SEQUENCE: 44
gggagaaaaa agccaacctt aatgc                                          25

<210> SEQ ID NO 45
<211> LENGTH: 29
<212> TYPE: DNA
<213> ORGANISM: Artificial sequence
<220> FEATURE:
<223> OTHER INFORMATION: Primer sequence

<400> SEQUENCE: 45
attaaacgat taccctgagg atgatatgc                                      29

<210> SEQ ID NO 46
<211> LENGTH: 23
<212> TYPE: DNA
<213> ORGANISM: Artificial sequence
<220> FEATURE:
<223> OTHER INFORMATION: Primer sequence

<400> SEQUENCE: 46
```

-continued

```
ggtgcgtttt cttcccatat tcc                                          23

<210> SEQ ID NO 47
<211> LENGTH: 27
<212> TYPE: DNA
<213> ORGANISM: Artificial sequence
<220> FEATURE:
<223> OTHER INFORMATION: Primer sequence

<400> SEQUENCE: 47
tcttttatat ccccttcgtc tgcaaac                                      27

<210> SEQ ID NO 48
<211> LENGTH: 24
<212> TYPE: DNA
<213> ORGANISM: Artificial sequence
<220> FEATURE:
<223> OTHER INFORMATION: Primer sequence

<400> SEQUENCE: 48
gttaaatggt ggtggtgcat tcac                                         24

<210> SEQ ID NO 49
<211> LENGTH: 23
<212> TYPE: DNA
<213> ORGANISM: Artificial sequence
<220> FEATURE:
<223> OTHER INFORMATION: Primer sequence

<400> SEQUENCE: 49
gcggtccaag gaattttgct aac                                          23

<210> SEQ ID NO 50
<211> LENGTH: 25
<212> TYPE: DNA
<213> ORGANISM: Artificial sequence
<220> FEATURE:
<223> OTHER INFORMATION: Primer sequence

<400> SEQUENCE: 50
caaacacccc ttattccagt caaac                                        25

<210> SEQ ID NO 51
<211> LENGTH: 25
<212> TYPE: DNA
<213> ORGANISM: Artificial sequence
<220> FEATURE:
<223> OTHER INFORMATION: Primer sequence

<400> SEQUENCE: 51
ccactttttc ccaacccccaa aattc                                       25

<210> SEQ ID NO 52
<211> LENGTH: 23
<212> TYPE: DNA
<213> ORGANISM: Artificial sequence
<220> FEATURE:
<223> OTHER INFORMATION: Primer sequence

<400> SEQUENCE: 52
gcagacccaa gtttcctttc tcc                                          23

<210> SEQ ID NO 53
<211> LENGTH: 20
<212> TYPE: DNA
```

<213> ORGANISM: Artificial sequence
<220> FEATURE:
<223> OTHER INFORMATION: Primer sequence

<400> SEQUENCE: 53
cggttcccac gaaaagcaac                                            20

<210> SEQ ID NO 54
<211> LENGTH: 25
<212> TYPE: DNA
<213> ORGANISM: Artificial sequence
<220> FEATURE:
<223> OTHER INFORMATION: Primer sequence

<400> SEQUENCE: 54
cactgagcaa cacaattgga ctttc                                      25

<210> SEQ ID NO 55
<211> LENGTH: 23
<212> TYPE: DNA
<213> ORGANISM: Artificial sequence
<220> FEATURE:
<223> OTHER INFORMATION: Primer sequence

<400> SEQUENCE: 55
cctggcttat caccttggac ttc                                        23

<210> SEQ ID NO 56
<211> LENGTH: 24
<212> TYPE: DNA
<213> ORGANISM: Artificial sequence
<220> FEATURE:
<223> OTHER INFORMATION: Primer sequence

<400> SEQUENCE: 56
tgtcttgggt gggtttctct taac                                       24

<210> SEQ ID NO 57
<211> LENGTH: 21
<212> TYPE: DNA
<213> ORGANISM: Artificial sequence
<220> FEATURE:
<223> OTHER INFORMATION: Primer sequence

<400> SEQUENCE: 57
cccagactcc tcccttgttt c                                          21

<210> SEQ ID NO 58
<211> LENGTH: 23
<212> TYPE: DNA
<213> ORGANISM: Artificial sequence
<220> FEATURE:
<223> OTHER INFORMATION: Primer sequence

<400> SEQUENCE: 58
acctcagcca ttgaactcac ttc                                        23

<210> SEQ ID NO 59
<211> LENGTH: 25
<212> TYPE: DNA
<213> ORGANISM: Artificial sequence
<220> FEATURE:
<223> OTHER INFORMATION: Primer sequence

<400> SEQUENCE: 59
ctgctctact ggtttcccta gattc                                      25

<210> SEQ ID NO 60
<211> LENGTH: 24
<212> TYPE: DNA
<213> ORGANISM: Artificial sequence
<220> FEATURE:
<223> OTHER INFORMATION: Primer sequence

<400> SEQUENCE: 60
ccataaccag actcagcaga gaac                                          24

<210> SEQ ID NO 61
<211> LENGTH: 22
<212> TYPE: DNA
<213> ORGANISM: Artificial sequence
<220> FEATURE:
<223> OTHER INFORMATION: Primer sequence

<400> SEQUENCE: 61
caaacccacc gcagtaactt ac                                            22

<210> SEQ ID NO 62
<211> LENGTH: 19
<212> TYPE: DNA
<213> ORGANISM: Artificial sequence
<220> FEATURE:
<223> OTHER INFORMATION: Primer sequence

<400> SEQUENCE: 62
gcctgcccag gacttactc                                                19

<210> SEQ ID NO 63
<211> LENGTH: 21
<212> TYPE: DNA
<213> ORGANISM: Artificial sequence
<220> FEATURE:
<223> OTHER INFORMATION: Primer sequence

<400> SEQUENCE: 63
aggtatgtgg ctgctgtctt c                                             21

<210> SEQ ID NO 64
<211> LENGTH: 18
<212> TYPE: DNA
<213> ORGANISM: Artificial sequence
<220> FEATURE:
<223> OTHER INFORMATION: Primer sequence

<400> SEQUENCE: 64
aaggaggcgt cgctgtac                                                 18

<210> SEQ ID NO 65
<211> LENGTH: 20
<212> TYPE: DNA
<213> ORGANISM: Artificial sequence
<220> FEATURE:
<223> OTHER INFORMATION: Primer sequence

<400> SEQUENCE: 65
gcagccagtc aactctgaac                                               20

<210> SEQ ID NO 66
<211> LENGTH: 21
<212> TYPE: DNA
<213> ORGANISM: Artificial sequence
<220> FEATURE:

```
<223> OTHER INFORMATION: Primer sequence

<400> SEQUENCE: 66
acagtcaccc tgcacactta c                                              21

<210> SEQ ID NO 67
<211> LENGTH: 16
<212> TYPE: DNA
<213> ORGANISM: Artificial sequence
<220> FEATURE:
<223> OTHER INFORMATION: Primer sequence

<400> SEQUENCE: 67
ccccgggtgc gaagtc                                                    16

<210> SEQ ID NO 68
<211> LENGTH: 21
<212> TYPE: DNA
<213> ORGANISM: Artificial Sequence
<220> FEATURE:
<223> OTHER INFORMATION: Primer sequence

<400> SEQUENCE: 68
tcagcacacc tatcggaaag c                                              21

<210> SEQ ID NO 69
<211> LENGTH: 21
<212> TYPE: DNA
<213> ORGANISM: Artificial Sequence
<220> FEATURE:
<223> OTHER INFORMATION: Primer sequence

<400> SEQUENCE: 69
cccagactcc tcccttgttt c                                              21
```

POLYMERIZATION OF NUCLEIC ACIDS USING ACTIVATION BY POLYPHOSPHOROLYSIS (APP) REACTIONS

CROSS REFERENCE TO RELATED APPLICATIONS

This application is a divisional of U.S. application Ser. No. 13/324,676, filed Dec. 13, 2011, now U.S. Pat. No. 8,932,813, and claims the benefit of priority under 35 U.S.C. §119(e) to U.S. Provisional Patent Application No. 61/422,477, filed 13 Dec. 2010, each of which are herein incorporated by reference in its entirety.

FIELD OF THE DISCLOSURE

This disclosure relates to methods for polymerization of nucleic acids using activation by polyphosphorolysis (APP) reactions, in the presence of improved polyphosphorylating agents.

BACKGROUND OF THE DISCLOSURE

This disclosure relates to methods for polymerization of nucleic acids (or nucleotides) using activation by polyphosphorolysis (APP) reactions. Polymerization may be carried out using primers having 3'-ends blocked with dideoxynucleotides in a reaction mixture containing a balance of pyrophosphate (PPi) and dNTP. These methods have been previously described in, for example, U.S. Pat. Nos. 6,534,269 B2, 7,033,763 B2, 7,238,480, 7,105,298, 7,504,221, and 7,919,253. Similar methods are also described in U.S. Pat. No. 7,745,125. These methods have many applications, including detection of rare alleles in the presence of wild type alleles (e.g., one mutant allele in the presence of $10^6$-$10^9$ wild type alleles). The methods are useful to, for example, detect minimal residual disease-causing agent(s) (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine). Other applications of such methods are known to those of skill in the art.

Those of skill in the art desire improved methods for carrying out such methods. It has been surprisingly found that several other compounds are also capable of deblocking of nucleic acids. Described herein are methods for performing an APP reaction using various polyphosphorolyzing agents. Advantages of these methods will be apparent from the following description of such improved methods.

BRIEF DESCRIPTION OF THE DRAWINGS

FIG. 3A is an amplification plot, FIG. 3B is a dissociation curve, and FIG. 3C depicts products run on an agarose gel.

FIG. 4A is an amplification plot, FIG. 4B is a dissociation curve, and FIG. 4C depicts products run on an agarose gel.

FIG. 6A is an amplification plot of triphosphate-catalyzed reactions and FIG. 6B is an amplification plot of PPi-catalyzed reactions. FIG. 6C is a melting curve of triphosphate-catalyzed reactions. FIG. 6D, FIG. 6E, and FIG. 6F are melting curves of PPi-catalyzed reactions.

FIG. 9A is a kinetic plot of linear amplification. FIG. 9B lists relative rates of linear amplifications of three reactions using perfectly matched substrates and mismatches substrates.

FIG. 12A is an amplification plot of tetraphosphate-initiated PCR. FIG. 12B depicts the polyphosphate tetraphosphate.

FIG. 13A depicts IDP-initiated PCR products run on an agarose gel. FIG. 13B depicts the polyphosphate imidodiphosphate (IDP).

FIG. 16A depicts an amplification plot for positive digital PCR (dPCR) using APP reactions and FIG. 16B depicts their dissociation curves. FIG. 16C depicts an amplification plot for negative dPCR using APP reactions and FIG. 16D depicts their dissociation curves.

FIG. 17A and FIG. 17C depict amplification plots for digital PCR using conventional dye-based master mix and FIG. 17B and FIG. 17D depict their dissociation curves, respectively.

FIG. 18A is a plot depicting the distribution of Ct's of negative reactions and positive reactions in digital PCR using APP and using conventional dye-based master mix. FIG. 18B is a plot to indicate the mean and 1× standard deviation for the data depicted in FIG. 18A.

SUMMARY OF THE DISCLOSURE

Figure 1:
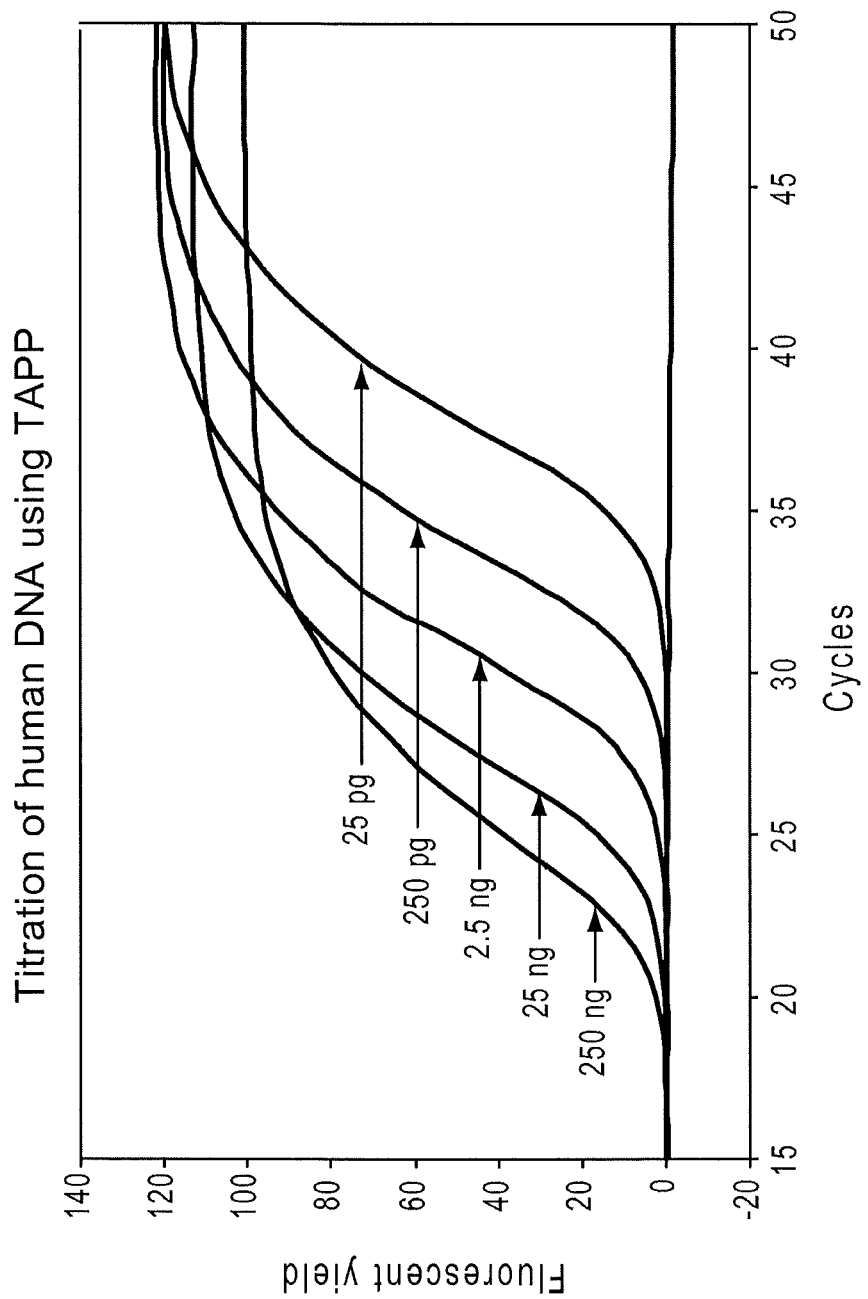
FIG. 1. Titration of human DNA using triphosphate-catalyzed APP.

Described herein are methods for amplifying a target nucleic acid from a test sample using activation by polyphosphorolysis (APP) reaction. In certain embodiments, APP is carried out using one or more polyphosphorolyzing agents. In some embodiments, the one or more polyphosphorolyzing agents may be represented by Formula I:

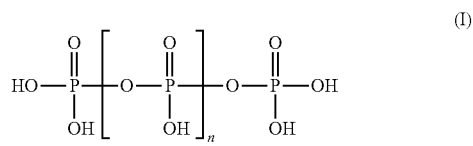

Wherein n is, for example, 1, 2, 3, 4, 5, 6, 7, 8, 9, or 10 or more. In some embodiments, the one or more polyphosphorolyzing agents may be represented by Formula II:

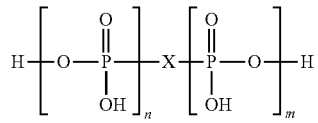

(II)

In some embodiments representing compounds of Formula II, n and/or m may be the same or different. And n and/or m may be, for example, 0, 1, 2, 3, 4, 5, 6, 7, 8, 9, or 10 with the proviso that n or m, but not both, may be 0. Thus, if n is 0, then m may be 1, 2, 3, 4, 5, 6, 7, 8, 9, or 10. If m is 0, then n may be 1, 2, 3, 4, 5, 6, 7, 8, 9, or 10. And both n and m may be 1, 2, 3, 4, 5, 6, 7, 8, 9, or 10. In some embodiments, n and m are both 1. In some embodiments, the sum of n and m is greater than or equal to 2 (e.g., n≥1 and m≥1, n≥2 and m≥0, n≥0 and m≥2). In some embodiments, such as where (but not limited to) the sum of n+m is greater than or equal to 2, X may be, for example,

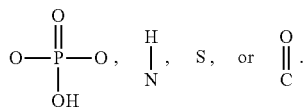

In some embodiments wherein the one or more polyphosphorolyzing agents are represented by Formula II, such as where (but not limited to) n or m=0, X may be, for example,

In some embodiments, the one or more polyphosphorolyzing agents may be:

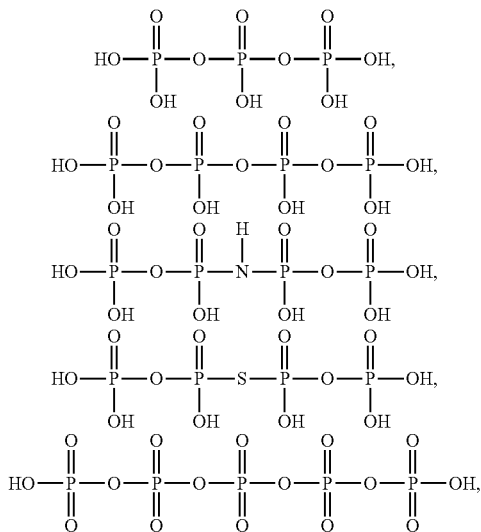

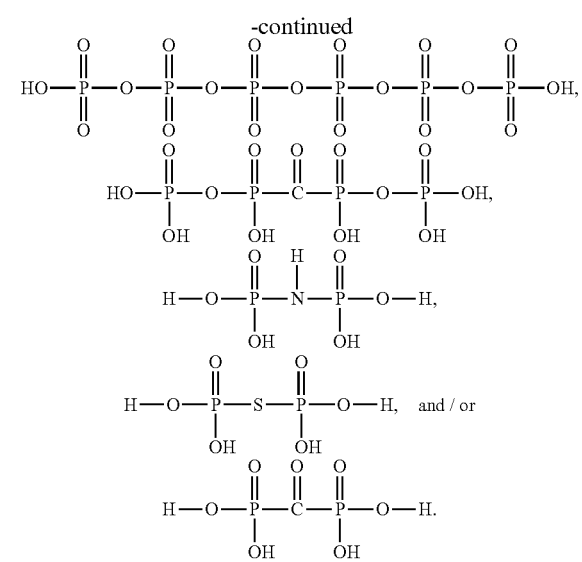

Any of the polyphosphorolyzing agents described herein may be combined with any other polyphosphorolyzing agents, such as those described herein. In some embodiments, the one or more polyphosphorolyzing agents may be pyrophosphate ($PP_i$) in combination with at least one or more other polyphosphorolyzing agents. Any of the one or more polyphosphorolyzing agents may be used in the form of a suitable salt (e.g., sodium). Typically, the reactions described herein further include an enzyme having polyphosphorolysis activity. Pyrophosphate has been described as a substrate for pyrophosphorolysis reaction in the literature (Kornberg, 1968), and in the U.S. Pat. Nos. 6,534,269 B2, 7,033,763 B2, 7,238,480, 7,105,298, 7,504,221, and 7,919,253, 7,745,1252 (all of which are incorporated by reference in their entirety into this application). APP is typically carried out by: (a) annealing to a nucleic acid a first oligonucleotide which has a non-extendable 3' end ("P*") removable by polyphosphorolysis (i.e., "activatable"); (b) removing the 3' non-extendable terminus using one or more polyphosphorolyzing agents and an enzyme having polyphosphorolysis activity to produce an unblocked oligonucleotide (i.e., "deblocking"); and, (c) extending the unblocked oligonucleotide to produce a desired nucleic acid strand. In some embodiments, methods are disclosed for producing an unblocked oligonucleotide from a blocked oligonucleotide (e.g., comprising a non-extendable 3' end removable by polyphosphorolysis), the method comprising contacting the blocked oligonucleotide (e.g., when hybridized to a target nucleic acid) with one or more polyphosphorolyzing agents. Such methods typically also include an enzyme having polyphosphorolysis activity. The enzyme having polyphosphorolysis activity for use in any of the methods described herein may be a DNA polymerase that may also be used to extend the unblocked oligonucleotide. In some embodiments, the enzyme may also have reverse transcriptase activity. In some embodiments, the polymerized or amplified nucleic acid is deoxyribonucleic acid (DNA). In some embodiments, the DNA is human DNA, bacteriophage DNA, plasmid DNA or synthetic DNA. In some embodiments, the method further comprises detecting the desired nucleic acid strand.

Variations of these methods, as well as reagents, kits, and devices for carrying out the same are also provided. Addi-

DETAILED DESCRIPTION

Described herein are methods for polymerizing, amplifying, and/or sequencing a target nucleic acid from a test sample using activation by polyphosphorolysis ("APP") reaction. Polyphosphorolysis refers to the removal of a non-extendable nucleotide from a nucleic acid (e.g., an oligonucleotide) in the presence of one or more polyphosphorylating agents and an enzyme that exhibits polyphosphorylating activity. APP may be used to polymerize and/or amplify and/or sequence nucleic acid molecules, including but not limited to ribonucleic acid (e.g., RNA) and/or deoxyribonucleic acid (e.g., DNA), or hybrids thereof. Other uses for the methods described herein will be readily understood by one of skill in the art.

In some embodiments, the one or more polyphosphorolyzing agents may be represented by Formula I:

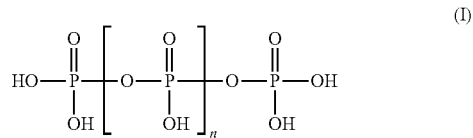

wherein n is, for example, 1, 2, 3, 4, 5, 6, 7, 8, 9, or 10, or more. In some embodiments, the one or more polyphosphorolyzing agents may be represented by Formula II:

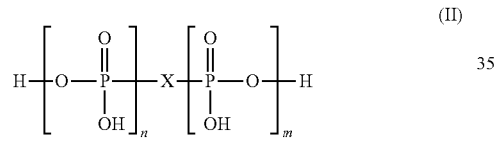

In some embodiments representing compounds of Formula II, n and/or m may be the same or different. And n and/or m may be, for example, 0, 1, 2, 3, 4, 5, 6, 7, 8, 9, or 10 with the proviso that n or m, but not both, may be 0. Thus, if n is 0, then m may be 1, 2, 3, 4, 5, 6, 7, 8, 9, or 10. If m is 0, then n may be 1, 2, 3, 4, 5, 6, 7, 8, 9, or 10. In some embodiments, n and m are both greater than or equal to 1. In some embodiments, n and m are both 1. In some embodiments, the sum of n+m is greater than or equal to 2 (e.g., $n \geq 1$ and $m \geq 1$, $n \geq 2$ and $m \geq 0$, $n \geq 0$ and $m \geq 2$). In some embodiments, such as where (but not limited to) the sum of n+m is greater than or equal to 2, X may be, for example,

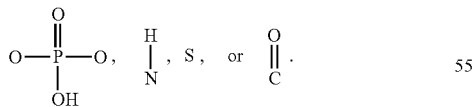

In some embodiments wherein the one or more polyphosphorolyzing agents are represented by Formula II, such as where (but not limited to) n or m=0, X may be, for example:

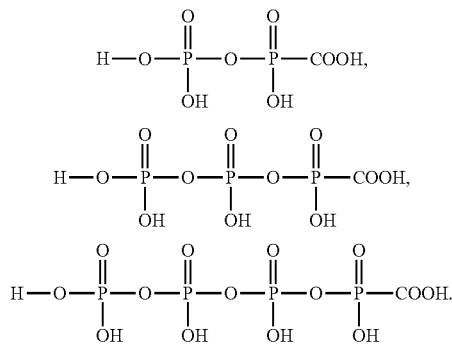

In some embodiments, the one or more polyphosphorolyzing agents may be:

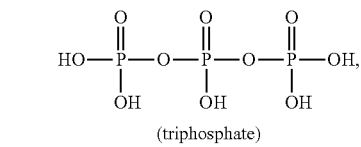
(triphosphate)

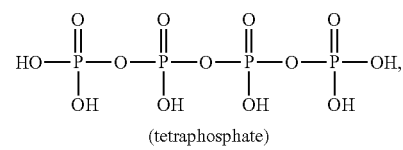
(tetraphosphate)

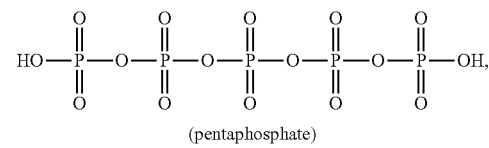
(pentaphosphate)

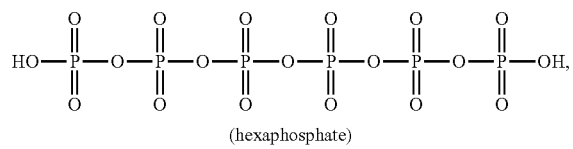
(hexaphosphate)

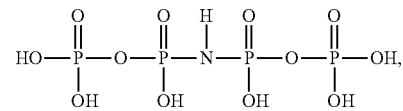

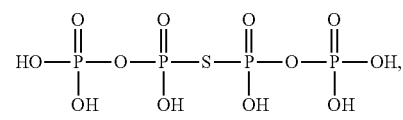

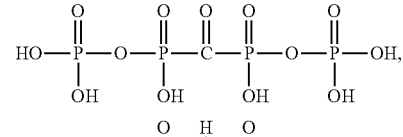

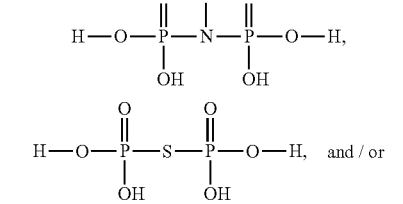

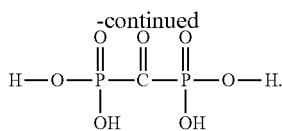

Any of the polyphosphorolyzing agents described herein may be combined with any other polyphosphorolyzing agents. In some embodiments, the one or more polyphosphorolyzing agents may be pyrophosphate ($PP_i$) in combination with at least one or more other polyphosphorolyzing agents. Any of the one or more polyphosphorolyzing agents may be used in the form of a salt (e.g., sodium). Typically, the reactions described herein further include one or more biocatalysts (e.g., enzyme(s)) having polyphosphorolysis activity to generate one or more nucleoside triphosphates. As shown above, for example, imidodiphosphate (IDP) links the phosphate moieties using nitrogen; similar diphosphate compounds may substitute sulfur for nitrogen. In some embodiments, a polyphosphate may be any phosphate ester having two or more phosphate moieties. In some embodiments, a polyphosphate may be any phosphate esters having three or more phosphate moieties.

An exemplary one or more biocatalyst that may be used in APP is a DNA polymerase that catalyzes polymerization of nucleoside triphosphates and polyphosphorolysis of duplexes of DNA in the presence of one or more polyphosphorolyzing agents as described herein. Exemplary DNA polymerases having polyphosphorolysis activity include but are not limited to thermostable Tfl, Taq, and/or genetically engineered DNA polymerases (e.g., AMPLITAQFS, THERMOSEQUENASE), those having the active site mutation F667Y or the equivalent of F667Y (e.g., in Tth) which shows improved affinity for dideoxynucleotide as incoming nucleotide (e.g., smaller $K_m$ for ddNTP)), RQ1 as described in U.S. Pat. No. 7,422,872 (incorporated by reference in its entirety into this application) and mutants thereof (e.g., RQY in which 669 is substituted by tyrosine, which may provide for reverse transcription and/or direct sequencing of RNA), THERMINATOR I (NEB), THERMINATOR II, THERMINATOR III, and/or THERMINATOR GAMMA (all available from NEB), among others. These and other potentially suitable DNA polymerases may be described in, for example, U.S. Pub. 2008/0254525A1, U.S. Pub. 2007/0020622A1, U.S. Pub. 2007/0009924A1, U.S. Pat. No. 4,889,818, U.S. Pat. No. 4,965,188, U.S. Pat. No. 5,047,342, U.S. Pat. No. 5,079,352, U.S. Pat. No. 5,270,179, U.S. Pat. No. 5,374,553, U.S. Pat. No. 5,436,149, U.S. Pat. No. 5,512,462, U.S. Pat. No. 5,614,365, and/or U.S. Pat. No. 6,228,628B1, all of which are hereby incorporated by reference in their entirety into this application. It has been found that the use of such genetically engineered DNA polymerases may improve the efficiency of APP.

APP provides for the extension of oligonucleotides by converting a non-extendable oligonucleotide into an extendable oligonucleotide, extending the oligonucleotide to produce a desired nucleic acid strand (e.g., a complementary copy of a target nucleic acid), and optionally amplifying and detecting the desired nucleic acid strand. A non-extendable nucleotide refers to a nucleotide, which upon incorporation into a nucleic acid prevents further extension of the nucleic acid, e.g., by at least one biocatalyst (e.g., enzyme). A nucleotide may be extendable by one enzyme, but non-extendable by another enzyme. A non-extendable nucleotide to one enzyme could become extendable or partially extendable under different conditions. An extendable nucleotide may refer to a nucleotide to which at least one other nucleotide can be added or covalently bonded at a 3'-position of the sugar moiety of the extendable nucleotide by a biocatalyst (e.g., enzyme) present in the reaction. Extension may also start from 2'-OH of a nucleotide which may or may not have an extendable 3'-OH. Extending a nucleic acid refers to the addition of or incorporation of one or more nucleotides to or into a given nucleic acid. An extended oligonucleotide is typically an oligonucleotide (e.g., a primer nucleic acid) to which one or more additional nucleotides have been added or otherwise incorporated (e.g., covalently bonded to). APP is typically carried out using the steps of: (a) annealing to a nucleic acid a first oligonucleotide which has a non-extendable 3' end ("P*") that is removable by polyphosphorolysis (i.e., activatable); (b) removing that 3' non-extendable terminus using a polyphosphorolyzing agent and a biocatalyst (i.e., a DNA polymerase) having polyphosphorolysis activity to produce an unblocked oligonucleotide; and, (c) extending the unblocked oligonucleotide to produce a desired nucleic acid strand. Further steps of detecting the desired nucleic acid strand may also be included as described below.

The one or more polyphosphorolyzing agents may be included in the reaction mixture at any suitable concentration. For instance, a suitable concentration may be approximately 1-500 µM. Other suitable polyphosphorolyzing agent concentrations ranges may include but are not limited to approximately 1-10 µM, 10-20 µM, 20-30 µM, 30-40 µM, 40-50 µM, up to 50 µM, 50-60 µM, 60-70 µM, 70-80 µM, 90-100 µM, up to 100 µM, 100-150 µM, 150-200 µM, up to 200 µM, 200-250 µM, 250-300 µM, up to 300 µM, 300-350 µM, 350-400 µM, up to 400 µM, 400-450 µM, 450-500 µM. Additionally suitable polyphosphorolyzing agent concentrations include but are not limited to 1 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 125 µM, 150 µM, 175 µM, 200 µM, 225 µM, 250 µM, 275 µM, 300 µM, 325 µM, 350 µM, 375 µM, 400 µM, 425 µM, 450 µM, 475 µM, and 500 µM. Particularly suitable concentrations of polyphosphorolyzing agent(s) may include but are not limited to approximately 25 µM, 40 µM, 50 µM, and 100 µM, 150 µM, 200 µM and 250 µM. Other suitable concentrations of polyphosphorolyzing agent may also be suitable as would be understood by one of skill in the art, and are also contemplated to be part of this description.

The methods described herein may be carried out in any of several different forms. In some embodiments, the method comprises the following steps carried out serially:
(a) Annealing to the template strand a complementary activatable oligonucleotide "P*". This activatable oligonucleotide has a non-extendable nucleotide at its 3' terminus. It has no nucleotides at or near its 3' terminus that mismatch the corresponding nucleotides on the template strand. Therefore, the terminal nucleotide is hybridized to the template strand when the oligonucleotide P* is annealed.
(b) Polyphosphorolyzing the annealed activatable oligonucleotide P* with at least one polyphosphorolyzing agent described herein and an enzyme that has polyphosphorolysis activity. This activates the oligonucleotide P* by removal of the hybridized terminal nucleotide.
(c) Polymerizing by extending the activated oligonucleotide P* on the template strand in presence of four nucleoside triphosphates and a nucleic acid polymerase to synthesize the desired nucleic acid strand.

The APP method may also be used to amplify a desired nucleic acid strand by, for example, adding the following additional steps: (d) separating the desired nucleic acid strand of step (c) from the template strand, and (e) repeating steps (a)-(d) until a desired level of amplification of the desired nucleic acid strand is achieved. Steps (a) to (c) of APP can be conducted sequentially as two or more temperature stages on a thermocycler, or they can be conducted as one temperature stage on a thermocycler.

As described above, APP may be used to amplify nucleic acid molecules, including but not limited to ribonucleic acid (e.g., RNA) and/or deoxyribonucleic acid (e.g., DNA). When used to amplify DNA, the non-extendable, activatable oligonucleotide P* is typically a 2'-deoxyoligonucleotide, the terminal deoxynucleotide may be a 2',3'-dideoxynucleotide, the four nucleoside triphosphates are 2'-deoxynucleoside triphosphates, and the nucleic acid polymerase is a DNA polymerase. The DNA polymerase used in step (c) can also be the enzyme having polyphosphorolysis activity used in step (b). Amplification by APP may be linear or exponential. Linear amplification is obtained when the activatable oligonucleotide P* is the only complementary oligonucleotide used. Exponential amplification is obtained when a second oligonucleotide is present that is complementary to the desired nucleic acid strand (e.g., as in PCR). The second oligonucleotide can either be an extendable or an activatable non-extendable oligonucleotide. The activatable oligonucleotide P* and the second oligonucleotide flank the region that is targeted for amplification. In step (a), the second oligonucleotide anneals to the separated desired nucleic acid strand product of step (d). In step (c), polymerization extends the second oligonucleotide on the desired nucleic acid strand to synthesize a copy of the nucleic acid template strand. In step (d), the synthesized nucleic acid template strand is separated from the desired nucleic acid strand. Steps (a) through (d) may then be repeated until the desired level exponential amplification has been achieved.

In certain embodiments, the APP method is used for allele-specific amplification. The nucleic acid template strand is typically a sense or antisense strand of one allele and is present in mixture with the corresponding (sense or antisense) nucleic acid strand of the second allele. The activatable (e.g., non-extendable) oligonucleotide P* has no mismatches near the 3' terminus of the first allelic strand and has at least one nucleotide at or near its 3' terminus that mismatches the corresponding nucleotide of the second allelic strand. Because of the mismatch, in step (a) of the APP method the terminal non-extendable nucleotide of oligonucleotide P* is not hybridized to the second allele. In step (b), polyphosphorolysis does not substantially remove the non-hybridized terminal or near terminal nucleotide from the activatable oligonucleotide P* annealed to the second allele. In step (c), therefore, the oligonucleotide P* is not substantially extended by polymerization on the second allele. As a result, the desired nucleic acid strand of the first allele synthesized on the template strand is amplified preferentially over any nucleic acid strand synthesized on the second allele. In one embodiment, the APP method is used for exponential amplification of a rare, mutant allele in a mixture containing one or more wild-type alleles. Strands of the alleles may be separated to provide single-stranded DNA, followed by the serial steps (a)-(e):
 (a) Annealing to the sense or antisense strands of each allele a complementary activatable 2'-deoxyoligonucleotide P* that has a non-extendable 2',3'-dideoxynucleotide at its 3' terminus. P* has no nucleotides at or near its 3' terminus that mismatch the corresponding 2'-deoxynucleotides on the mutant strand, but has at least one nucleotide at or near its 3' terminus that mismatches the corresponding 2'-deoxynucleotide on the wild type strand. Consequently, the terminal 2',3'-dideoxynucleotide is hybridized to the mutant strand but not to the wild-type strand when the oligonucleotide P* is annealed. Simultaneously, a second 2'-deoxyoligonucleotide that is complementary to the anti-parallel strands of each allele is annealed to the anti-parallel strands. The activatable 2'-deoxyoligonucleotide P* and the second 2'-deoxyoligonucleotide flank the region of the gene to be amplified.
 (b) Polyphosphorolyzing the activatable P* that is annealed to a mutant strand with at least one polyphosphorolyzing agent and an enzyme that has polyphosphorolysis activity. This activates the P* that is annealed to the mutant strand by removal of the hybridized terminal 2',3'-dideoxynucleotide. It does not substantially activate the P* that is annealed to the wild-type strand because the non-hybridized terminal 2',3'-dideoxynucleotide is not substantially removed by the polyphosporolysis.
 (c) Polymerizing by extending the activated oligonucleotide P* on the mutant strand in presence of four nucleoside triphosphates and a DNA polymerase and simultaneously extending the second 2'-deoxyoligonucleotide on both mutant and wild-type anti-parallel strands.
 (d) Separating the extension products of step (c);
 (e) Repeating steps (a)-(d) until the desired level of exponential amplification of the mutant allele has been achieved.

The activatable P* is typically annealed to the antisense strands of the alleles and the second P* is annealed to the sense strands, or vice versa.

The methods described herein may also be used for scanning unknown sequence variants in a nucleic acid sequence or for re-sequencing of a predetermined sequence in a nucleic acid by carrying out the following steps serially:
 (a) Mixing under hybridization conditions a template strand of the nucleic acid with multiple sets of four activatable oligonucleotides P* which are sufficiently complementary to the template strand to hybridize therewith. Within each set, the oligonucleotides P* differ from each other in having a different 3'-terminal non-extendable nucleotide, so that the 3' terminal non-extendable nucleotide is hybridized to the template strand if the template strand is complementary to the 3' terminal non-extendable nucleotide. The number of sets corresponds to the number of nucleotides in the sequence to be interrogated.
 (b) Treating the resulting duplexes with at least one polyphosphorolyzing agent described herein and an enzyme that has polyphosphorolysis activity to activate by polyphosphorolysis only those oligonucleotides P* which have a 3' terminal non-extendable nucleotide that is hybridized to the template strand.
 (c) Polymerizing by extending the activated oligonucleotides P* on the template strand in presence of four nucleoside triphosphates and a nucleic acid polymerase.
 (d) Separating the nucleic acid strands synthesized in step (c) from the template strand.
 (e) Repeating steps (a)-(d) until a desired level of amplification is achieved, and (f) Arranging the nucleic acid sequence in order by analyzing overlaps of oligonuclotides P* that produced amplifications.

It is to be understood that the particular methods, reaction mixtures, and/or systems described herein may vary. The terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. As used in this specification and the appended claims, the singular forms "a", "an", and "the" also include plural referents unless the context clearly provides otherwise. All numerical ranges are intended to encompass each individual value within the range as if each were separately listed (e.g., 10-20 may include one or more of 10, 11, 12, 13, 14, 15, 16, 17, 18, 19 and/or 20). In terms of concentration ranges, these encompass fractional ranges, e.g., all values between 10-20 as if each were individually written out (e.g., 10.8, 11.5). The term "approximately", when used to modify a group of numerical values, is meant to apply to each value individually unless otherwise indicated.

An "amplicon" typically refers to a molecule made by copying or transcribing another molecule, e.g., as occurs in transcription, cloning, and/or in a polymerase chain reaction ("PCR") (e.g., strand displacement PCR amplification (SDA), duplex PCR amplification, etc.) or other nucleic acid amplification technique. Typically, an amplicon is a copy of a selected nucleic acid or a portion thereof (e.g., a template or target nucleic acid) or is complementary thereto. The term "amplifying" or "amplification" in the context of nucleic acids typically refers to the production of multiple copies of a polynucleotide, or a portion of the polynucleotide, typically starting from a small amount of the polynucleotide (e.g., a single polynucleotide molecule), where the amplification products or amplicons are generally detectable. Any of several methods may be used to amplify the target nucleic acid from the sample. The term "amplifying" which typically refers to an "exponential" increase in target nucleic acid is being used herein to describe both linear and exponential increases in the numbers of a select target sequence of nucleic acid. The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. Exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., WO 2006/081222), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990) and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al. Nat. Genet. 19: 225-232 (1998); and/or Banér et al. Nucleic Acid Res., 26: 5073-5078 (1998)), and strand displacement amplification (SDA) (Little, et al. Clin Chem 45:777-784 (1999)), among others. Many systems are suitable for use in amplifying target nucleic acids and are contemplated herein as would be understood by one of skill in the art.

Any of several methods may be used to detect APP-amplified target nucleic acids using various primers and/or probes. Many different reagents, systems, and/or detectable labels may be used in the methods described herein. These include, for example, TaqMan® systems, detectable label-quencher systems (e.g., FRET, salicylate/DTPA ligand systems (see, e.g., Oser et al. Angew. Chem. Int. Engl. 29(10): 1167 (1990), displacement hybridization, homologous probes, assays described in EP 070685), molecular beacons (e.g., NASBA), Scorpion, locked nucleic acid (LNA) bases (Singh, et al. Chem Commum 4:455-456 (1998)), peptide nucleic acid (PNA) probes (Pellestor, et al. European J. Human Gen. 12:694-700 (2004)), Eclipse probes (Afonina, et al. Biotechniques 32:940-949 (2002)), light-up probes (Svanvik, et al. Anal Biochem 281:26-35 (2001)), molecular beacons (Tyagi, et al. Nat. Biotechnol. 14:303-308 (1996)), tripartite molecular beacons (Nutiu, et al. Nucleic Acids Res. 30:e94 (2002)), QuantiProbes (www.qiagen.com), HyBeacons (French, et al. Mol. Cell. Probes 15:363-374 (2001)), displacement probes (Li, et al. Nucleic Acids Res. 30:e5 (2002)), HybProbes (Cardullo, et al. PNAS 85:8790-8794 (1988)), MGB Alert (www.nanogen.com), Q-PNA (Fiandaca, et al. Genome Res. 11:609-611 (2001)), Plexor (www.Promega.com), LUX primers (Nazarenko, et al. Nucleic Acids Res. 30:e37 (2002)), Scorpion primers (Whitcombe, et al. Nat Biotechnol 17:804-807 (1999)), AmpliFluor (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress. An apparatus for detecting the signal generated by the detectable label may be used to detect, measure, and quantify the signal before, during, and/or after amplification. The particular type of signal may dictate the choice of detection method. For example, in some embodiments, fluorescent dyes are used to label probes and/or amplified products. The probes bind to single-stranded and/or double-stranded amplified products, and/or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence may be quantitated using standard equipment such as a spectra-fluorometer, for example. The use of other methods and/or reagents is also contemplated herein as would be understood by one of skill in the art.

One exemplary method for amplifying and detecting target nucleic acids is commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900). TaqMan® assays are typically carried out by performing nucleic acid amplification on a target polynucleotide using a nucleic acid polymerase having 5'-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked Taqman® assay) are known in the art and would be suitable for use in the methods described herein.

Another exemplary system utilizes double-stranded probes in displacement hybridization methods (see, e.g., Morrison et al. Anal. Biochem., 18:231-244 (1989); and/or Li, et al. Nucleic Acids Res., 30(2, e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for amplifying and detecting target nucleic acids involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher dye that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for amplifying RNA to double stranded DNA without temperature cycling. A NASBA reaction typically requires avian myeloblastosis virus reverse transcriptase (AMV-RT or AMV), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpion system is another exemplary assay format that may be used in the methods described herein. Scorpion primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., HEG monomer) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpion system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for molecular beacons are known in the art and would be suitable for use in the methods described herein.

One or more detectable labels and/or quenching agents are typically attached to an oligonucleotide (e.g., P*), primer and/or probe. The detectable label may emit a signal when free or when bound to the target nucleic acid. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorophore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels may also be used (see, e.g., US Pub. No. 2009/0197254), as would be known to those of skill in the art.

Nucleic acid binding agents may also be used to detect nucleic acids amplified using the methods described herein. Many suitable detectable nucleic acid binding agents are available to one of skill in the art and may be used alone or in combination with other agents and/or components of an assay system. Exemplary DNA binding agents may include, for example, acridines (e.g., acridine orange, acriflavine), actinomycin D (Jain, et al. J. Mol. Biol. 68:21 (1972)), anthramycin, BOBO™-1, BOBO™-3, BO-PRO™-1, cbromomycin, DAPI (Kapuseinski, et al. Nuc. Acids Res. 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, 1990, Nuc. Acids Res. 18:3753-3762), Hoechst 33342, homidium, JO-PRO™-1, LIZ dyes, LO-PRO™-1, mepacrine, mithramycin, NED dyes, netropsin, 4'6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX blue, SYTOX green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reaction by amplifying the target sequence in the presence of the dye, exciting the biological sample with light at a wavelength absorbed by the dye and detecting the emission therefrom; and, determining a melting profile of the amplified target sequence. The presence of amplified products and, therefore, the target sequence in the sample, may thereafter be determined by, for example, performing a melting curve analysis (e.g., non-linear least squares regression of the sum of multiple gaussians). It is to be understood that the use of the SYBR® Green dye is presented as an example, and that many such dyes may be used in the methods described herein. Other nucleic acid binding agents may also be suitable as would be understood by one of skill in the art.

Nucleic acids "hybridize" or "anneal" in a base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotides is typically base specific, e.g., A/T and G/C, by Watson/Crick and/or Hoogsteen-type interactions. It is not a requirement that two polynucleotides have 100% complementarity over their full length to achieve hybridization. In some aspects, a hybridization complex can form from intermolecular interactions, or alternatively, can form from intramolecular interactions. Hybridization occurs due to a variety of well-characterized forces, including hydrogen bonding, solvent exclusion, and base stacking An extensive guide to nucleic hybridization may be found in, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

A "mixture" refers to a combination of two or more different components. A "reaction mixture" refers a mixture that comprises molecules that can participate in and/or facilitate a given reaction or assay. To illustrate, an amplification reaction mixture generally includes a solution containing reagents necessary to carry out an amplification reaction, and typically contains primers, a biocatalyst (e.g., a nucleic acid polymerase, a ligase, etc.), dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components, which includes the biomolecules of the invention.

A "moiety" or "group" refers to one of the portions into which something, such as a molecule, is or can be divided (e.g., a functional group, substituent group, or the like). For example, an oligonucleotide described herein includes at least one donor moiety and/or at least one acceptor moiety in certain embodiments.

The term "mutation" refers to a nucleic acid that has been altered in its nucleic acid sequence or an encoded protein product of a nucleic acid that has been altered in its amino acid sequence relative to an unaltered or native form of the nucleic acid or encoded protein product. Such alterations include, for example, point mutations or substitutions, deletions and insertions.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), locked nucleic acids (LNA™), and the like. In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, a primer, etc. A nucleic acid may be, e.g., single-stranded, double-stranded, triple-stranded (and the like) and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) Chem. Soc. Rev. pp 169-176, which is incorporated by reference). To further illustrate, although a nucleic acid will generally contain phosphodiester bonds, in some cases nucleic acid analogs are included that have alternate backbones. These may include, without limitation, phosphoramide (Beaucage et al. (1993) Tetrahedron 49(10): 1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Brill et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365: 566; and Carlsson et al. (1996) Nature 380:207). Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which are each incorporated by reference. Several nucleic acid analogs are also described in, e.g., Rawls, C & E News Jun. 2, 1997 page 35. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. For instance, certain bases used in nucleotides that act as melting temperature ($T_m$) modifiers are optionally included. Exemplary of these are 7-deazapurines (e.g., 7-deazaguanine, 7-deazaadenine, and the like); pyrazolo[3,4-d]pyrimidines, propynyl-dN (e.g., propynyl-dU, propynyl-dC, and the like); hypoxanthine; inosine; xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil; non-naturally occurring bases as described by, for example, Seela et al. ((1991) Helv. Chim. Acta 74:1790; (1999) Helv. Chim. Acta 82:1640); Grein et al. ((1994) Bioorg. Med. Chem. Lett. 4:971-976), U.S. Pat. Nos. 5,484,908, 5,645,985, 5,990,303, 5,830,653, 6,639,059, 6,303,315, U.S. Pat. Appln. No. 2003/0092905, and the like.

"Nucleoside" typically refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, and the like. A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside. Nucleoside triphosphates and 2'-deoxynucleoside triphosphates or their chemically modified versions may be used as substrates for multiple-nucleotide extension by APP where, for example, one nucleotide is incorporated the extending strand can be further extended. 2',3'-dideoxynucleoside triphosphates, chemically modified versions thereof, or other suitable compounds (e.g., as in US 2005/0037398A1, acycloNMP) may be used as terminators for further extension may be used for single-nucleotide extension. Further examples of 2'-terminated NTPs are described in U.S. Pat. No. 7,745,125 B2, which is hereby incorporated by reference in its entirety. 2',3'-dideoxynucleoside triphosphates may be labeled with radioactivity or fluorescence dye for differentiation from the 3' terminal dideoxynucleotide of oligonucleotide P*. Mixtures of nucleoside triphosphates or 2'-deoxynucleoside triphosphates and 2',3'-dideoxynucleoside triphosphates may also be used.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases (e.g., RQY polymerase described above), telomerases, polynucleotide phosphorylases, and the like. A "thermostable enzyme" refers to an enzyme that is stable to heat, is heat resistant, and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known to persons skilled in the art and are exemplified in, for example, U.S. Pat. Nos. 4,683,202, 4,683,195, and 4,965,188. To further illustrate, a "thermostable polymerase" refers to an enzyme that is suitable for use in a temperature cycling reaction, such as a polymerase chain reaction ("PCR"). For a thermostable polymerase, enzymatic activity refers to the catalysis of the combination of the nucleotides in the proper manner to form primer extension products that are complementary to a template nucleic acid. Exemplary thermostable polymerases are described herein, and others may available to the skilled artisan may also be suitable.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Typically, the 3' end linkage of P* is a phosphodiester bond. Oligonucleotides may be prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. ((1979) Meth. Enzymol. 68:90-99); the phosphodiester method of Brown et al. ((1979) Meth. Enzymol. 68:109-151); the diethylphosphoramidite method of Beaucage et al. ((1981) Tetrahedron Lett. 22:1859-1862); the triester method of Matteucci et al. ((1981) J. Am. Chem. Soc. 103:3185-3191); automated synthesis methods; or the solid support method described in U.S. Pat. No. 4,458,066, and/or other methods known to those skilled in the art.

As described above, "P*" represents an oligonucleotide having a non-extendable 3' end ("P*") that is removable by polyphosphorolysis. A P* oligonucleotide may also be referred to as "activatable", in that removal of the non-extendable 3' end renders the oligonucleotide suitable for polymerization (e.g., "activated P*"). The non-extendable 3' end of a P* oligonucleotide may be a dideoxynucleotide, an acyclonucleotide, a terminator having a 3'-hydroxyl but being 2' modified with a bulky molecule to prevent extension from the 3'-OH (e.g., US 2007/0154914A1), or a "virtual" terminator having modification(s) at the base to prevent extension from the 3'OH' by AmpliTaqFS (Wu, et al Nucleic Acids Research, 35(19): 6339-6349 (2007)). Other forms of P* are also contemplated and may be of use in the methods described herein, as would be understood by one of skill in the art.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide). Although other primer nucleic acid lengths are optionally utilized, they typically comprise hybridizing regions that range from about 8 to about 100 nucleotides in length. Shorter primer nucleic acids generally require lower temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid may be labeled, if desired, by incorporating a detectable label as described herein.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under selected hybridization conditions. A hybridization assay carried out using a probe under sufficiently stringent hybridization conditions permits the selective detection of a specific target sequence. The term "hybridizing region" refers to that region of a nucleic acid that is exactly or substantially complementary to, and therefore capable of hybridizing to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support. A probe of the invention may be generally included in a nucleic acid that comprises one or more labels (e.g., donor moieties, acceptor moieties, and/or quencher moieties), such as a 5'-nuclease probe, a hybridization probe, a fluorescent resonance energy transfer (FRET) probe, a hairpin probe, or a molecular beacon, which can also be utilized to detect hybridization between the probe and target nucleic acids in a sample. In some embodiments, the hybridizing region of the probe is completely complementary to the target sequence. However, in general, complete complementarity is not necessary (e.g., nucleic acids can be partially complementary to one another); stable hybridization complexes may contain mismatched bases or unmatched bases. Modification of the stringent conditions may be necessary to permit a stable hybridization complex with one or more base pair mismatches or unmatched bases. Sambrook et al., Molecular Cloning: A Laboratory Manual, 3rd Ed., Cold Spring Harbor Laboratory Press, Cold Spring Harbor, N.Y. (2001) provides guidance for suitable modification. Stability of the target/probe hybridization complex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

The methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, or spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. The kit typically includes at least a pair of oligonucleotides (e.g., at least one of the pair being a P* oligonucleotide) for amplifying at least one target nucleic acid from a sample, one or more polyphosphorolyzing agents described herein, a biocatalyst (e.g., DNA polymerase) and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. Other embodiments of particular systems and kits are also contemplated which would be understood by one of skill in the art.

Certain embodiments are further described in the following examples. These embodiments are provided as examples only and are not intended to limit the scope of the claims in any way. All references cited within this application are incorporated by reference in their entirety into this application.

EXAMPLES

Example 1

Titration of Human DNA with Triphosphate

Human DNA template titrations were performed with and without the presence of human genomic DNA. FIG. 1 shows the amplification curves in the presence of 250 ng, 25 ng, 2.5 ng, 250 pg, and 25 pg of human DNA and non-template control (NTC) (to test for non-specific amplification). These data illustrate that dye-based detection of amplification may be achieved using triphosphate-catalyzed reactions. The reactions were performed using an ABI 7900 Sequence Detection System with the following temperature profile: 50 cycles of 95° C. for 3 seconds, then 65° C. for 60 seconds. Each 20 μl-reaction contained 50 mM Tris (pH 8.25), 1× EvaGreen, 31 μM dNTPs, 3 mM MgCl$_2$, 60 mM KCl, Tween 0.1%, 40 μM triphosphate (pentasodium triphosphate, Sigma-Aldrich cat. No. 72061), 10 pg/μl Taq FY mutant DNA polymerase 10A per 100 μl reaction, 500 nM PA-1F (5'-CATCCTGGTTTGTGTTTTGCCTAA(ddC)-3'; SEQ ID NO.: 1), 500 nM PA-1R (5'-GGGAGAAAAAAGC-CAACCTTAATG(ddC)-3' SEQ ID NO.: 2), and Human DNA (Cat. No. #403062, Life Technologies, Carlsbad, Calif.) at the designated concentrations.

Example 2

Titration of Human DNA Using Power SYBR

Figure 2:
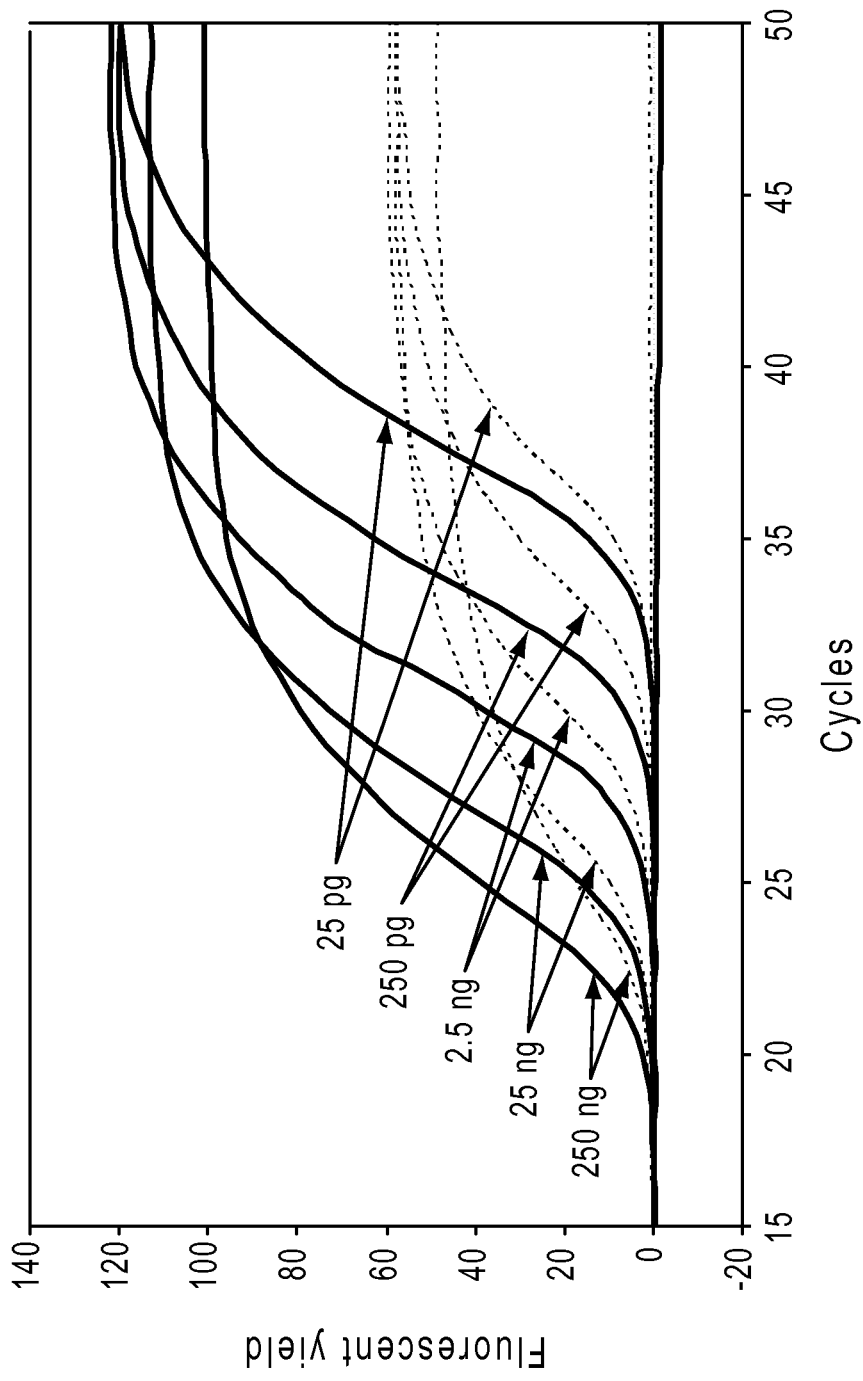
FIG. 2. Comparison of triphosphate-catalyzed APP with SYBR Green I based assay.

Human DNA template titrations were performed with and without the presence of human genomic DNA with ABI's Power SYBR. FIG. 2 shows the amplification curves using Power SYBR (dash lines) in the presence of 250 ng, 25 ng, 2.5 ng, 250 pg, and 25 pg of human DNA and non-template control (NTC) (to test for non-specific amplification) in comparison with triphosphate-catalyzed reactions (solid lines) performed as described in Example 1. These data illustrate that the triphosphate-catalyzed reactions may provide improved $C_T$ and/or signal strength. The SYBR Green reactions were performed using an ABI 7900 Sequence Detection System with the following temperature profile: 50 cycles of 95° C. for 3 seconds, then 60° C. for 60 seconds. Each 20 μL-reaction contained 1× Power SYBR master mix (Cat. No. #4385372, Life Technologies, Carlsbad, Calif.), 500 nM PA-1F (5'-CATCCTGGTTTGTGTTTTGC-CTAAC-3'; SEQ ID NO.: 1), 500 nM PA-1R (5'-GGGA-GAAAAAAGCCAACCTTAATGC-3' SEQ ID NO.: 2), and Human DNA (Cat. No. #403062, Life Technologies, Carlsbad, Calif.) at the designated concentrations.

Example 3

Amplification of a Plasmid Template by Power SYBR

Figure 3A:
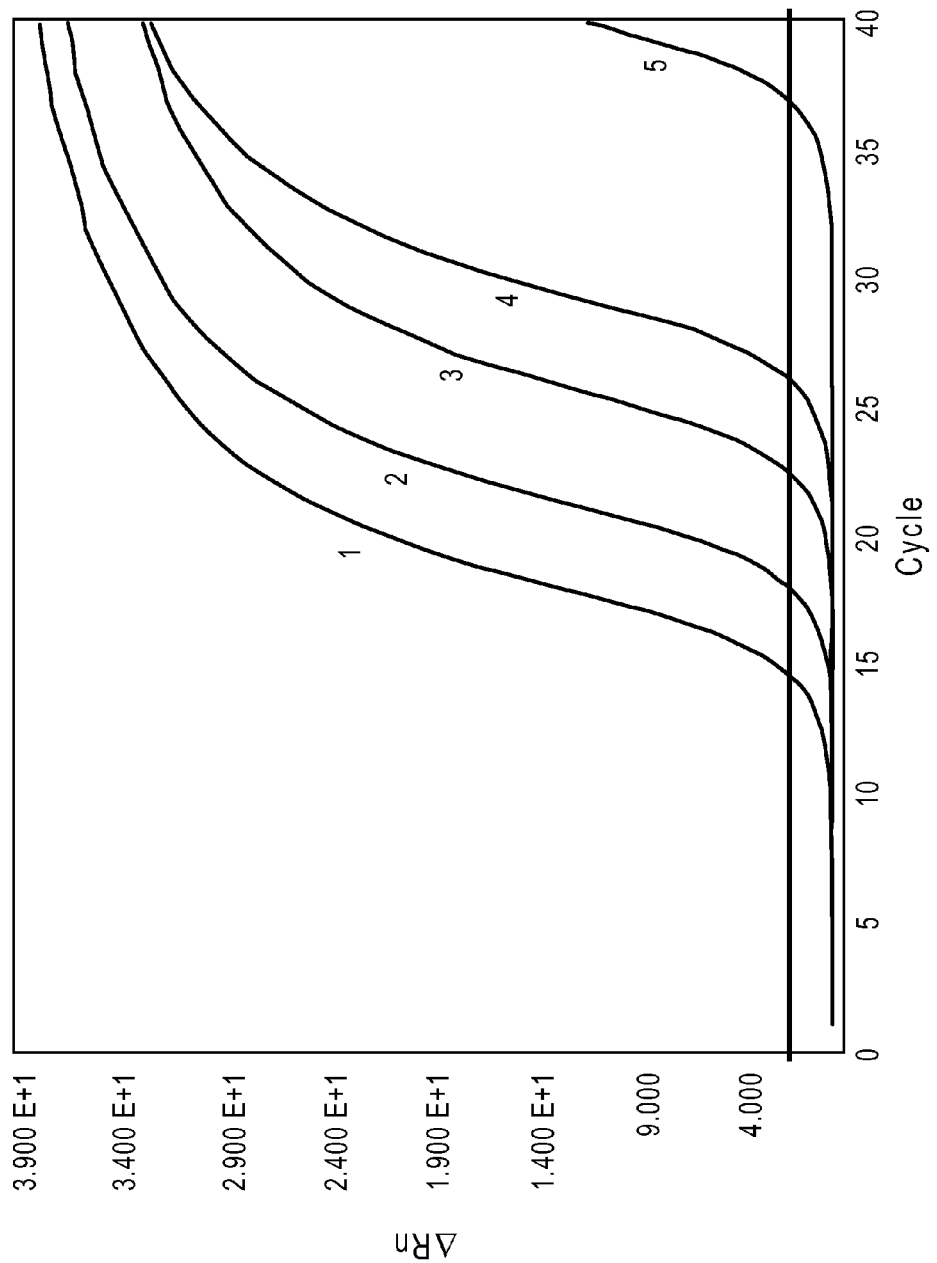
FIGS. 3A, 3B and 3C. Examples of amplification from a plasmid by Power SYBR.
Figure 3B:
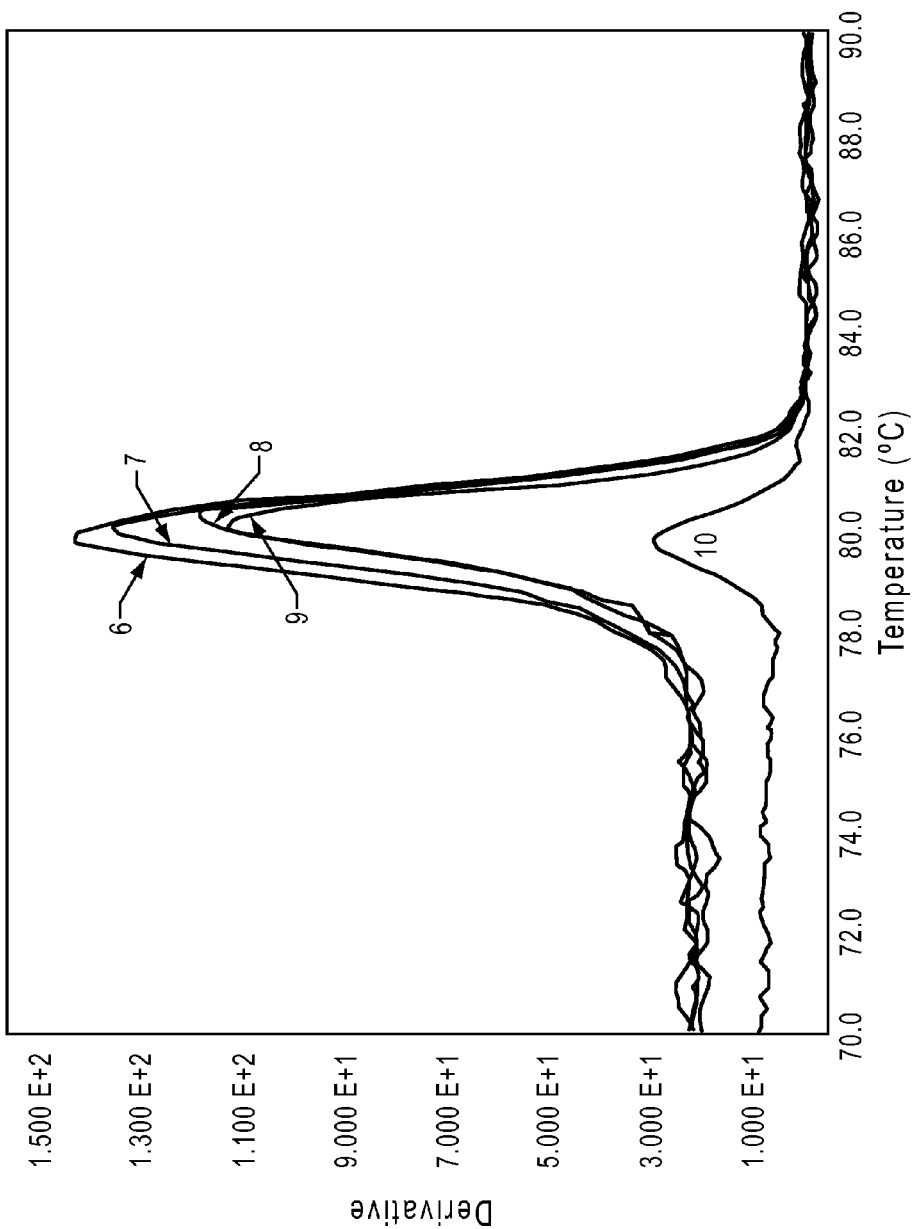
Figure 3C:
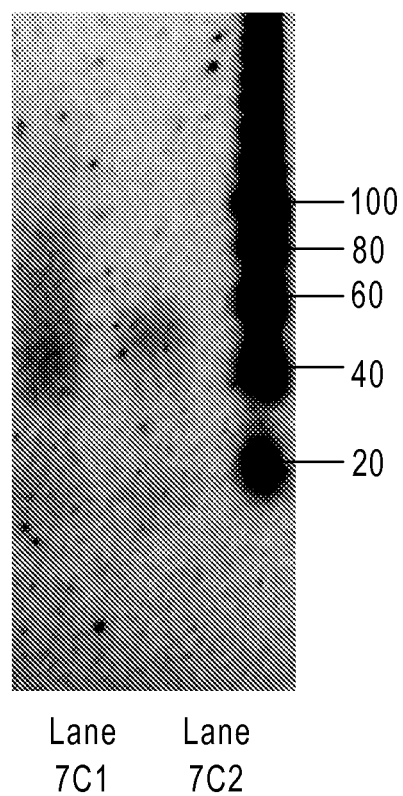

A titration of a plasmid DNA was performed with ABI's Fast SYBR. The result showed that the master mix did not yield a specific product. FIGS. 3A-C shows the amplification curves using Fast SYBR in the presence of 1 μL of undiluted plasmid prep (trace 1), 10-fold diluted plasmid prep (trace 2), 100 fold diluted plasmid prep (trace 3), 1000 fold diluted plasmid prep (trace 4), and a NTC (trace 5) performed as described following a thermal profile as described in Example 1. Melting curves are shown in FIG. 3B, in which traces 6, 7, 8, 9, and 10 correspond to the amplifications represented by traces 1-5, respectively, of FIG. 3A. FIG. 3C illustrates an agarose gel electrophoresis image of the PCR reactions shown by traces 1 (Lane 7C1) and 5 (Lane 7C2). The Fast SYBR reactions were performed using an ABI 7900 Sequence Detection System with the following temperature profile: 40 cycles of 95° C. for 3 seconds, then 60° C. for 60 seconds. Each 20 μl reaction contained 1× Fast SYBR master mix, 500 nM vD-primer: TGCAATACCGTGAGCTGACCC (SEQ ID NO.: 3), 500 nM v1699LR primer: GTCTGGTTGAAACGAGTGT-GCAGGC (SEQ ID NO.: 4), and about ten million copies of p540D plasmid DNA (a pUC-based plasmid containing an insert of the sequence of SEQ ID NO.: 7). The sequence amplified from plasmid 540D is TGCAATACCGTGAGCT-GACCCgtctgcgttcgacctacatcg acccactgccggacctgattcatc-cacgtac cggccGCCTGCACACTCGTTTCAACCAGAC (SEQ ID NO.: 5) (primers bind at capitalized sequence).

Example 4

Triphosphate-Catalyzed APP Amplification from Plasmid DNA

Figure 4A:
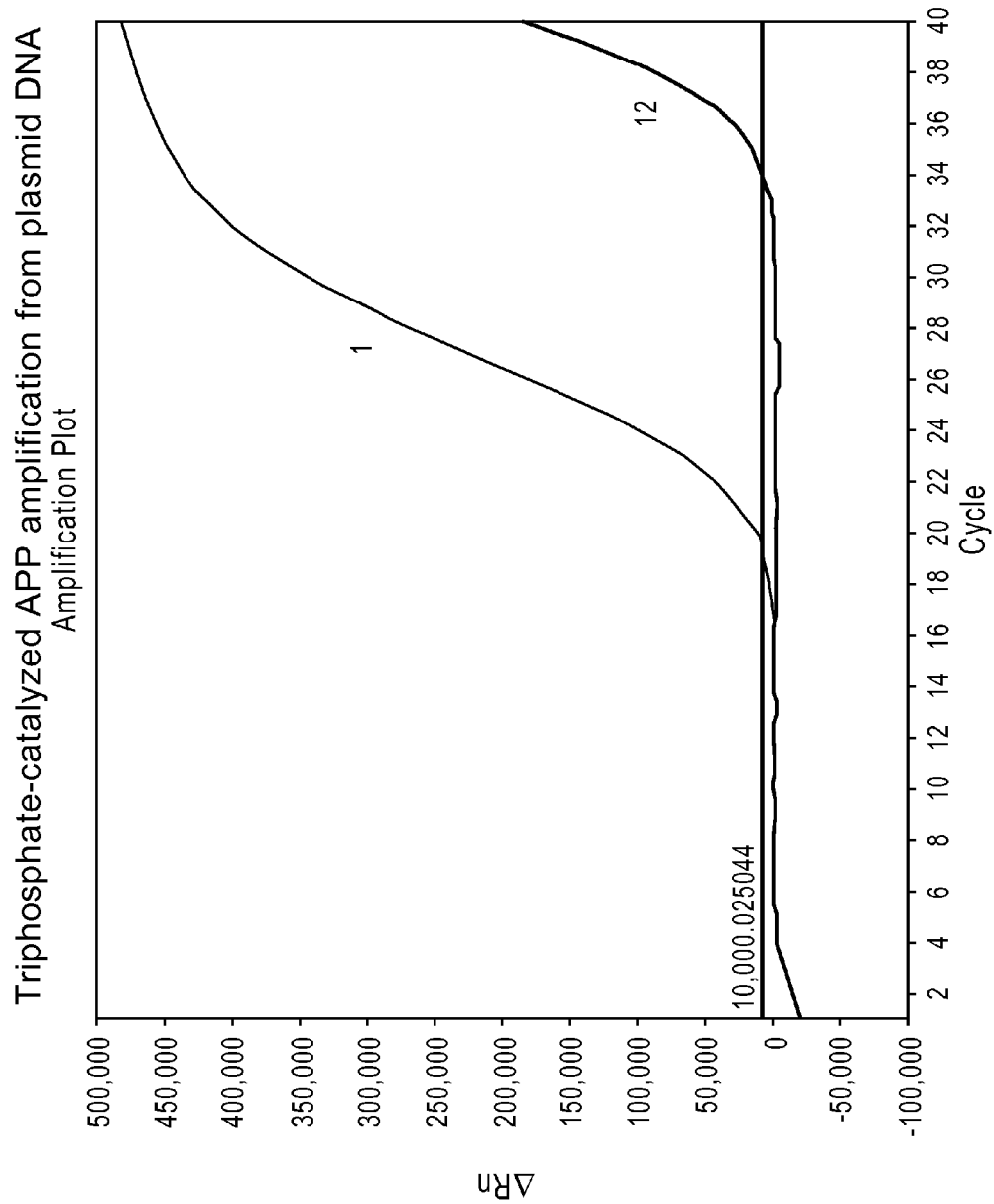
FIGS. 4A, 4B, and 4C. Examples of triphosphate-catalyzed APP amplification from plasmid DNA.
Figure 4B:
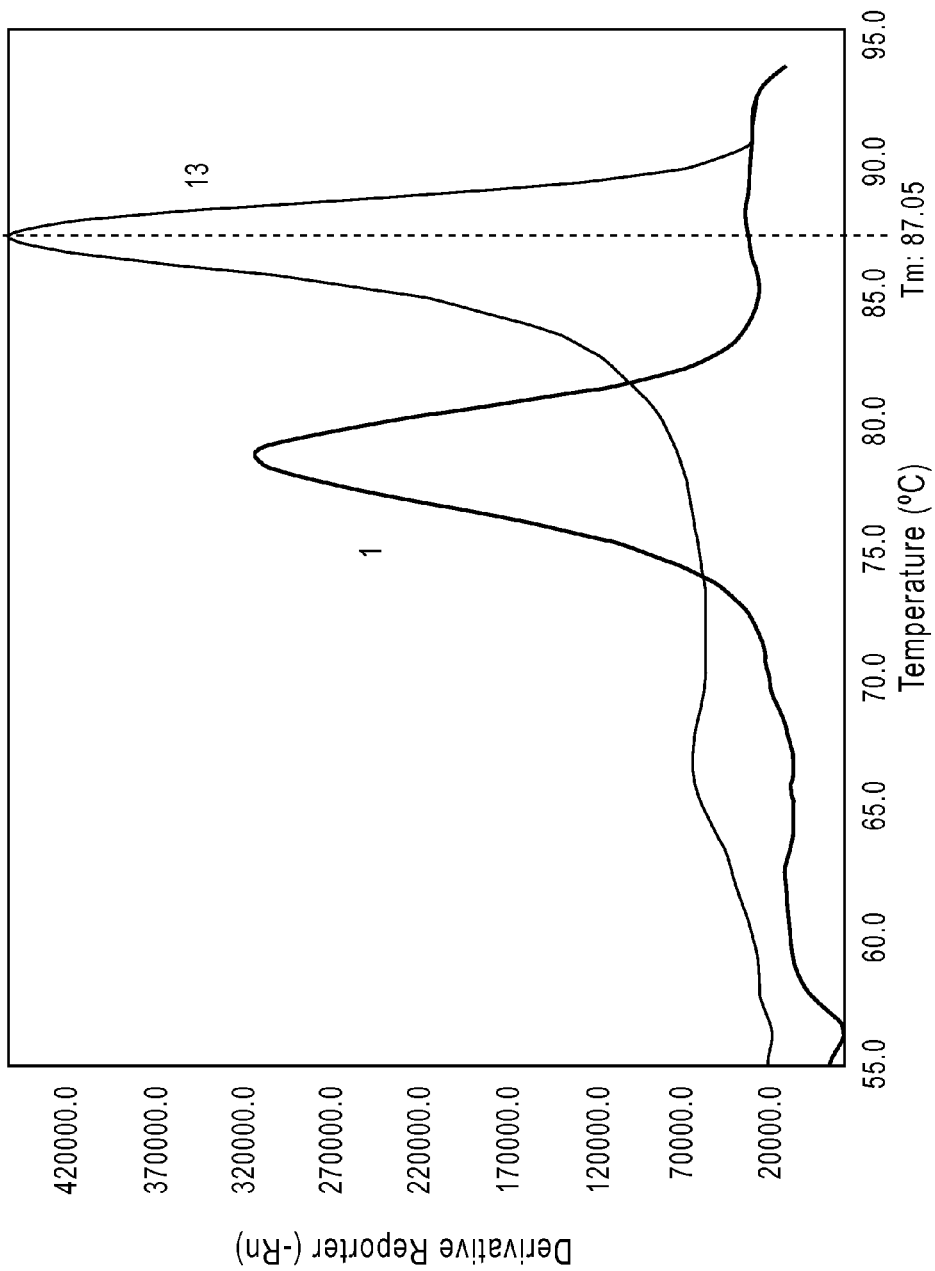
Figure 4:
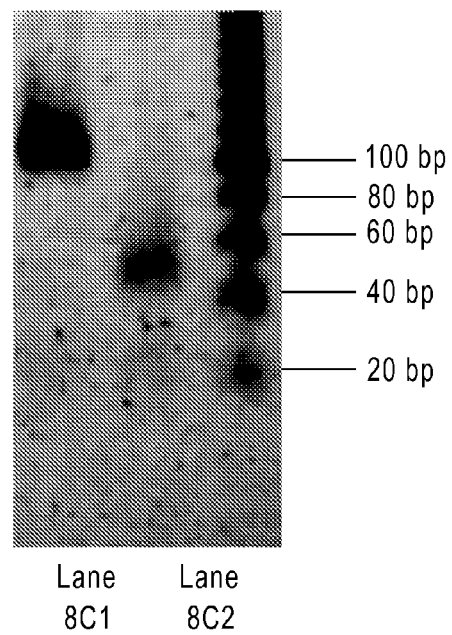

In contrast to the SYBR Green I reaction described in Example 3, triphosphate-catalyzed amplification of the aforementioned plasmid DNA (p540D) using ddC-terminated primers yields specific product. More specifically, the ddC-terminated primers for the reactions are TGCAATAC-CGTGAGCTGACC(ddC) (D primer, SEQ ID NO.: 3) and GTCTGGTTGAAACGAGTGTGCAGG(ddC) (1699LR primer, SEQ ID NO.: 4). Each 20 µL-reaction contained 50 mM Tris (pH 8), 1× EvaGreen, 31 µM dNTP, 2.5 mM MgCl$_2$, Tween 0.1%, 50 µM triphosphate, 10 pg/µl 10A (a F667Y mutation of Taq DNA polymerase) per 100 µl reaction, 500 nM D-primer, 500 nM 1699LR primer, and about ten million copies of p540D plasmid DNA. The triphosphate-catalyzed reactions were performed using an ABI 7900 Sequence Detection System with the following temperature profile: 40 cycles of 95° C., 3 seconds, then 65° C., 60 seconds. The results are shown in FIGS. 4A-C. The amplification curve from plasmid DNA is shown by Trace 11 in FIG. 4A, and the melting curve is shown by Trace 13 in FIG. 4B. The specific product generated by the reaction is shown in Lane 8C1 of an agarose gel electrophoresis in FIG. 4C. The results demonstrated that triphosphate-catalyzed reaction is more specific and stringent than the PowerSYBR PCR Products (e.g., as shown in FIGS. 3A-C).

Example 5

Comparison of Triphosphate-Catalyzed Reactions and PPi-Catalyzed Reactions

Figure 5:
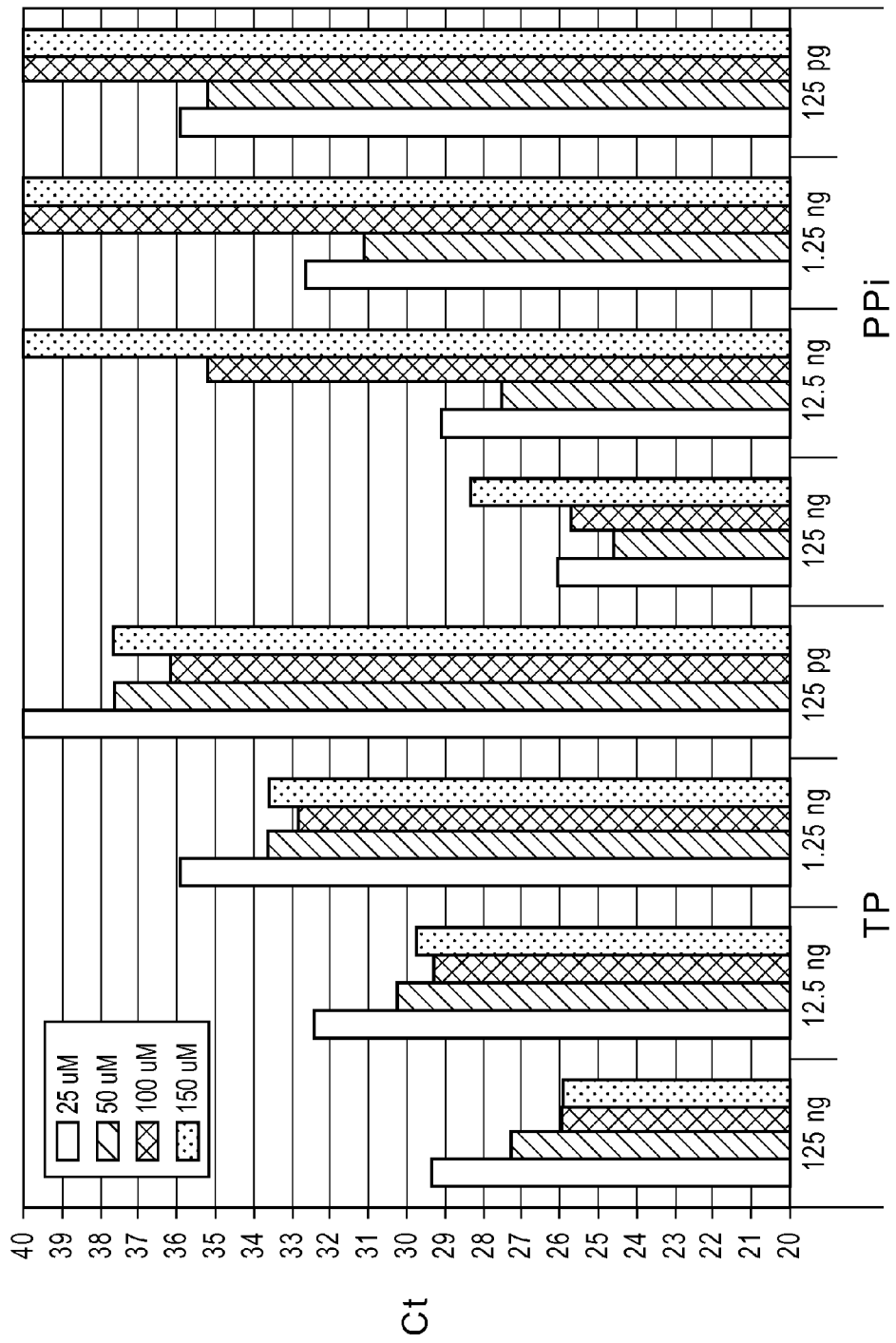
FIG. 5. Comparison of triphosphate- and PPi-catalyzed reactions using PA-10.
Figure 6A:
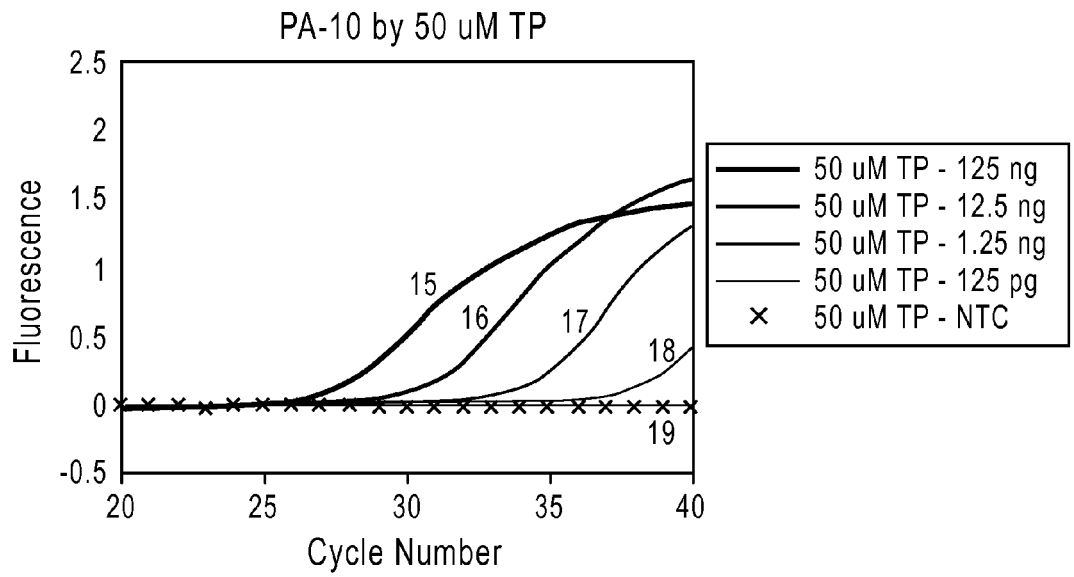
FIGS. 6A, 6B, 6C, 6D, 6E and 6F. Exemplary amplification curves and melting curves of triphosphate- and PPi-catalyzed reactions.
Figure 6B:
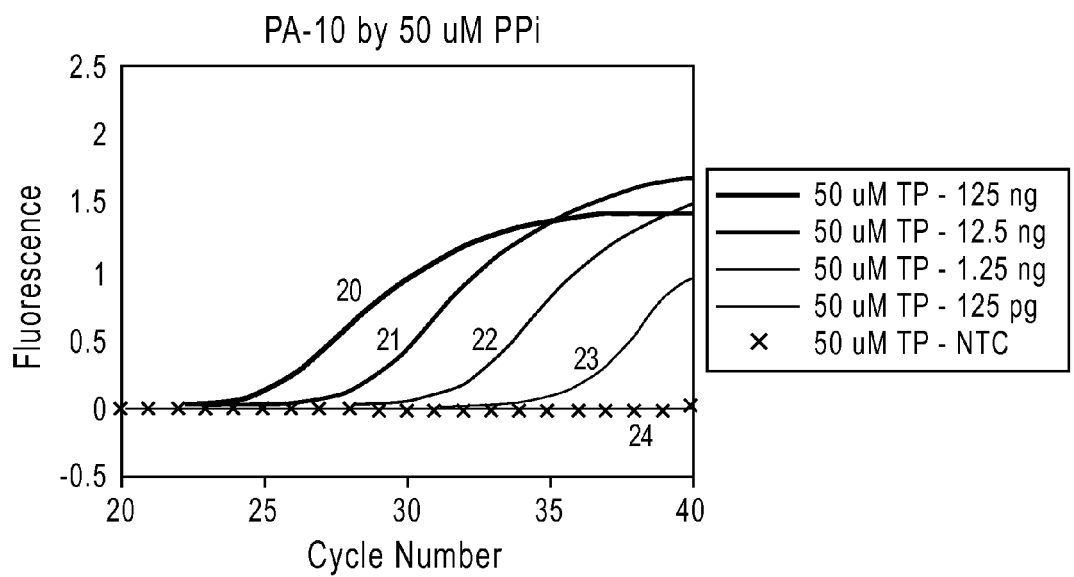
Figure 6C:
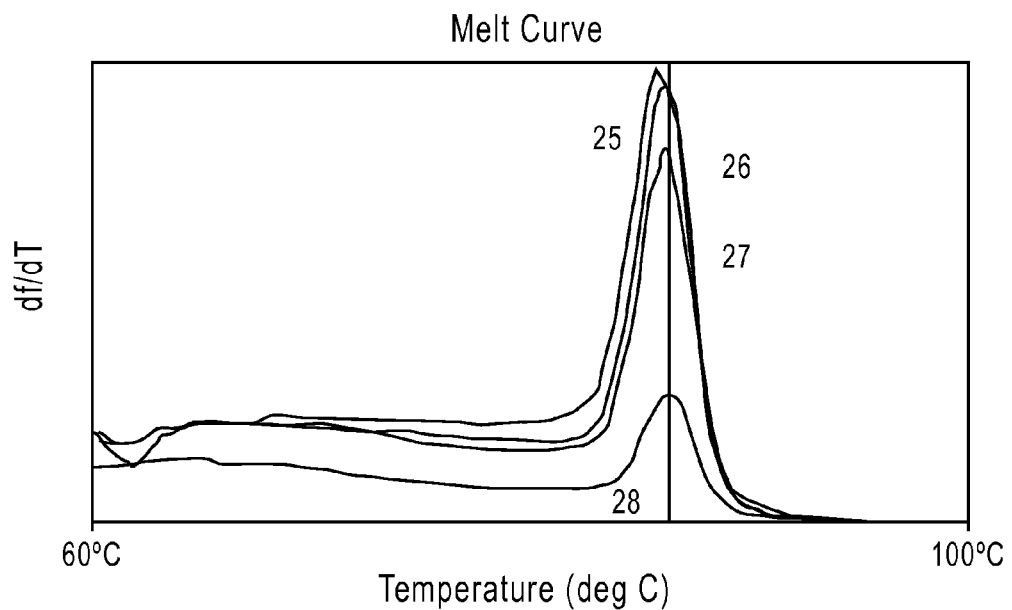
Figure 6D:
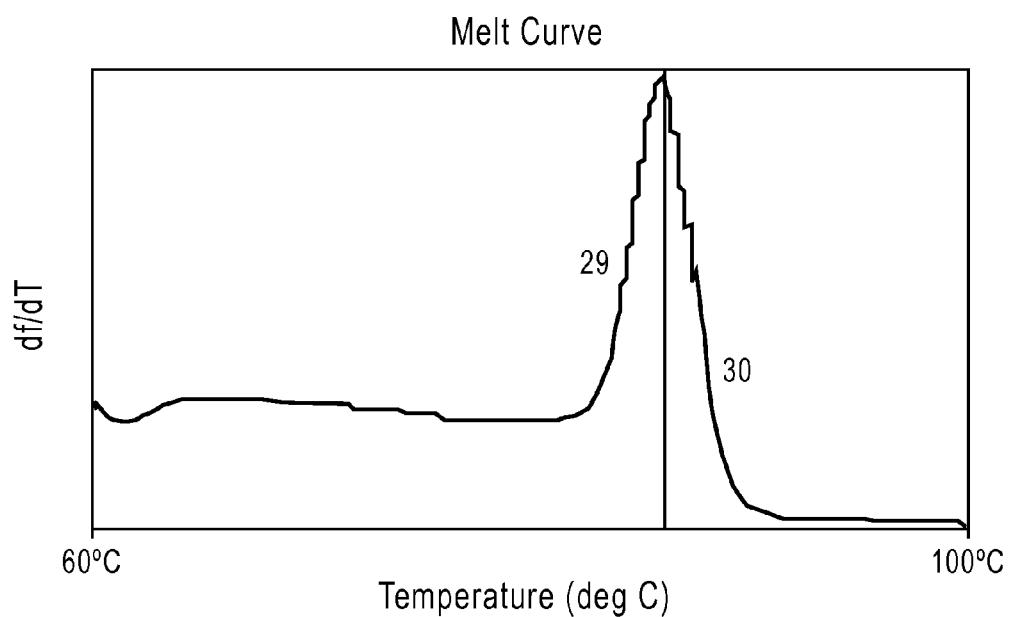
Figure 6E:
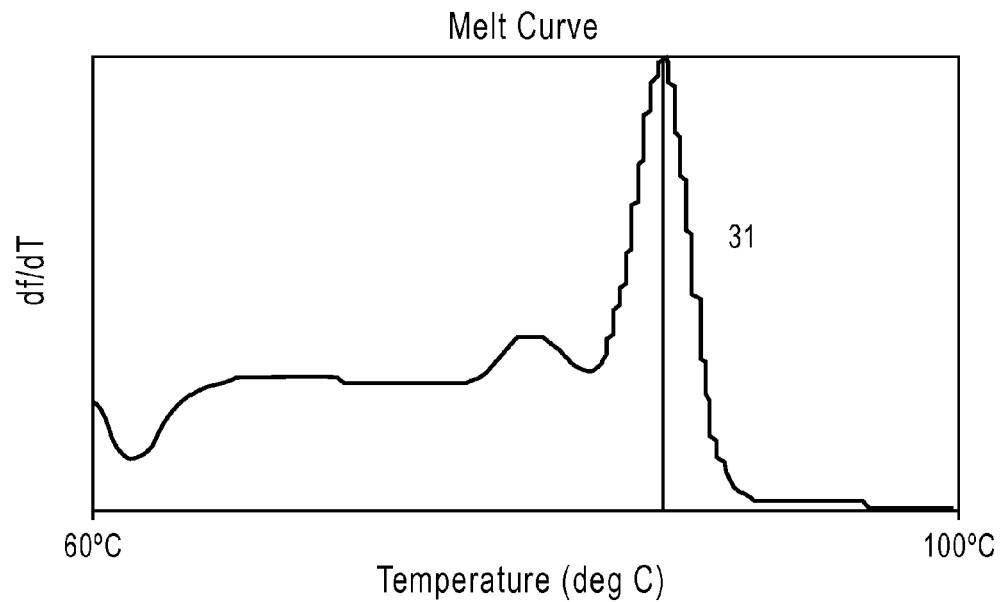
Figure 6F:
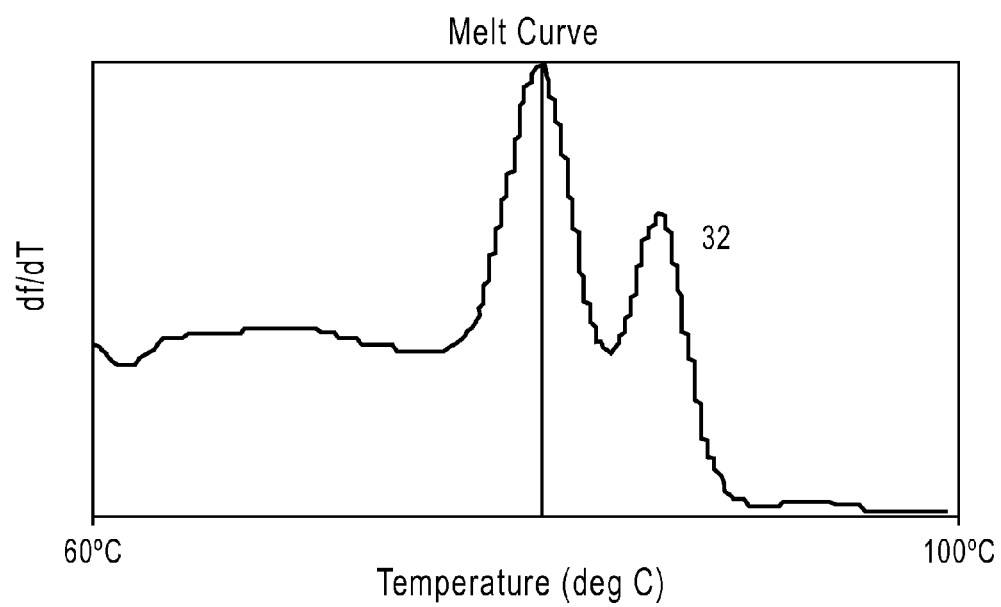
Figure 7:
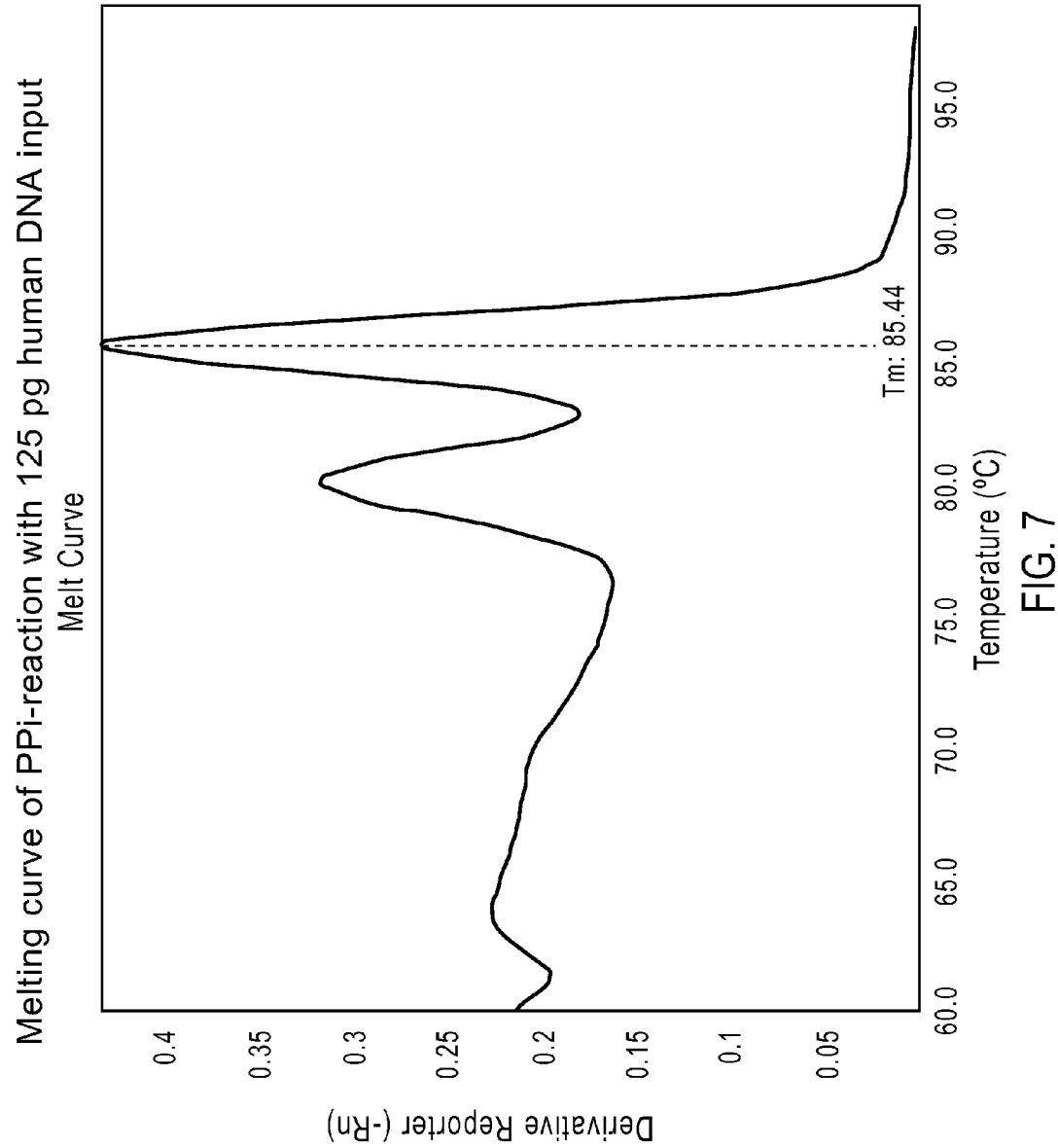
FIG. 7. Melting curve of PPi-catalyzed reaction with 125 pg human DNA input.

A comparison between triphosphate and PPi was performed using titrations of human DNA using primers PA-10F (GCATAGCAGTCCCCAAGAATGA (ddC); SEQ ID NO.: 6) and PA10R (CGGTTCCCACGAAAAGCAAC (ddC); SEQ ID NO.: 7). These primers were designed to generate a 127 bp amplicon from the human DNA template. Each 20 µl triphosphate-catalyzed reaction contained 50 mM Tris (pH 8); 1× EvaGreen; 31 uM dNTP; 2.5 mM MgCl$_2$; Tween 0.1%; 25, 50, 100, or 150 uM triphosphate; 10 pg/µl 10A per 100 uL reaction; 500 nM PA-10F; 500 nM PA-10R; and 125 ng, 12.5 ng, 1.25 ng, 125 pg, or 0 ng of human DNA. PP$_i$-catalyzed reactions were identically designed as the triphosphate-reactions except that PP$_i$ was used instead of triphosphate. The titration reactions were performed using an ABI 7900 Sequence Detection System with the following temperature profile: 40 cycles of 95° C., 3 seconds, then 60° C., 60 seconds. A melt analysis was performed following amplification by PCR. The $C_T$ of the titration using the various concentrations of PP$_i$ and triphosphate are plotted in FIG. 5. PP$_i$ showed inhibition at concentrations of 100 µM and 150 µM, while triphosphate did not show significant inhibition at any of these tested concentrations. The amplification curves under 50 µM triphosphate and 50 µM of PP$_i$ are shown in FIGS. 6A/C and 6B/D/E, respectively. The melting curves of the triphosphate reactions (FIG. 6C) demonstrate that all products were clean products. In contrast, the melting curves of PP$_i$ reaction for 1.25 ng human DNA (FIG. 6E) and 125 pg human DNA (FIG. 6F) exhibit non-specific peaks in addition to the specific peak. It should be noted that 50 µM PPi gave the most efficient reactions among the concentrations of PP$_i$ tested. However, this concentration gave non-specific reactions at low input DNA. At 25 µM PPi, non-specific product was observed for 125 pg input human DNA (FIG. 7). On the other hand, 100 and 150 µM PP$_i$ greatly inhibit amplifications when the input DNA concentrations were low. For this amplicon, PP$_i$ did not exhibit an optimal concentration at which the reaction was both efficient and specific.

Example 6

Comparison of Triphosphate-Catalyzed Reactions and PPi-Catalyzed Reactions

Figure 8:
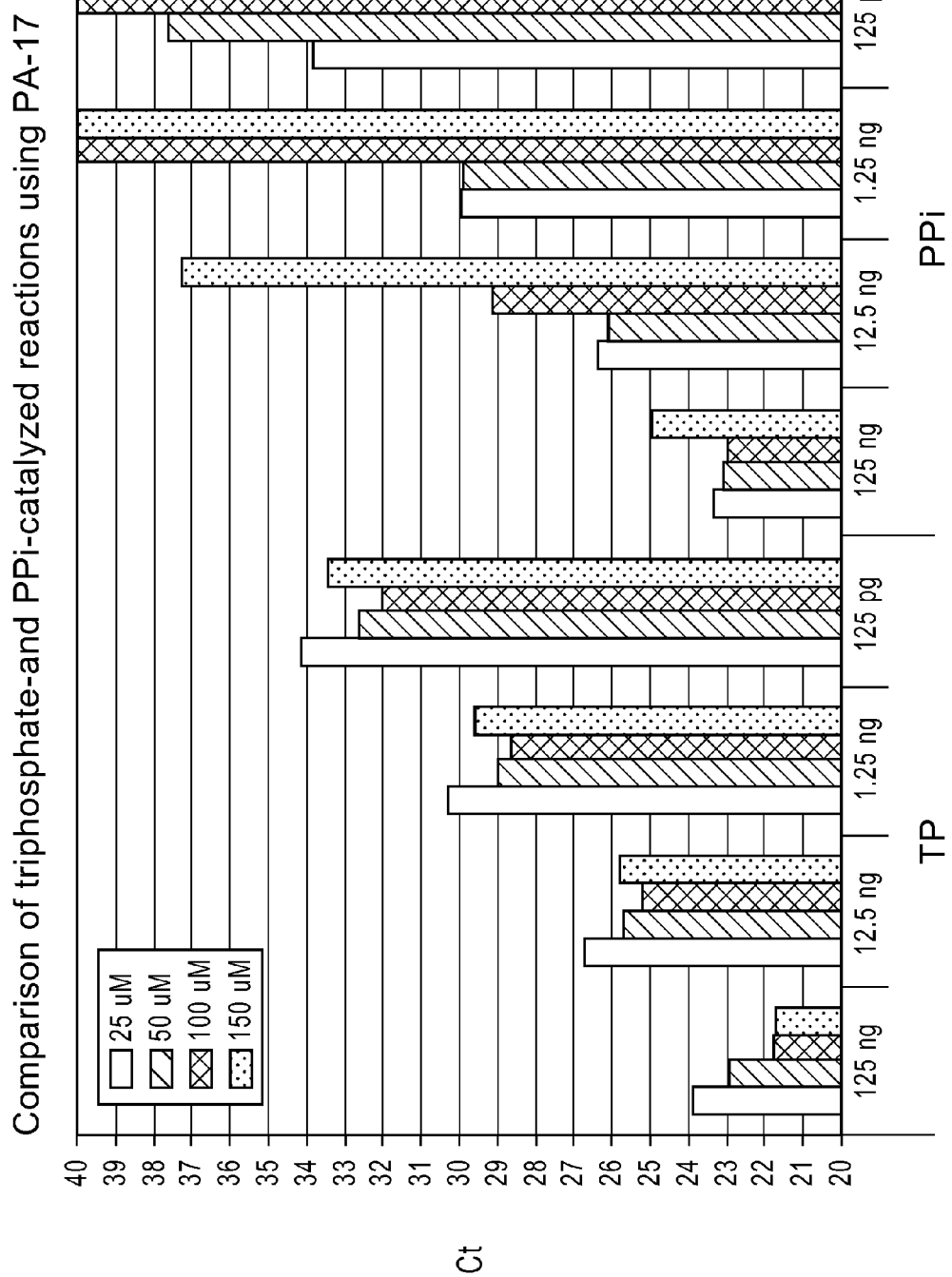
FIG. 8. Comparison of triphosphate- and PPi-catalyzed reactions using PA-17.

A comparison between triphosphate and PP$_i$ was performed using titrations of human DNA using primers PA-17F (GCTCCAGACAGAAACACCGTA(ddC); SEQ ID NO.: 8) and PA-17R (CCATAACCAGACTCAGCAGA-GAA(ddC); SEQ ID NO.: 9). The primers were designed to generate a 108 bp amplicon from the human DNA template. Triphosphate-reactions and PPi-reactions were conducted as described for the reactions of Example 5. The $C_T$ of the titration at the various concentrations of PP$_i$ and triphosphate are shown in FIG. 8. PP$_i$ exhibited inhibition at concentrations of 100 µM and 150 µM as demonstrated by the failed reactions in low input DNA, while triphosphate did not show significant inhibition at these tested concentrations.

Example 7

Comparison of Triphosphate-Catalyzed and PPi-Catalyzed Reactions

Linear amplifications are a convenient way to compare reaction rates. Here we employed fluorogenic substrates which generate fluorogenic signals once they were converted from partial duplex to substantially full duplex. This example demonstrated that triphosphate-initiated deblocking is more stringent than PP$_i$-initiated deblocking reactions.

Four substrates described in this example were made as detailed below:

(1) Primer vPA1F (5'-CATCCTGGTTTGTGTTTTGC-CTAAC-3'; SEQ ID NO.: 1) was allowed to anneal to PAPbttm (5'-/TAM/CAGCGTGTGGTATGCG/FAM-dT/CGACGTTAGGCAAAACACAAACCAGGATG-3'; SEQ ID NO.: 10) to form a duplex as shown below as vSub(PM):

```
5'-CATCCTGGTTTGTGTTTTGCCTAAC-3'      (SEQ ID NO.: 1)
   |||||||||||||||||||||||||
3'-GTAGGACCAAACACAAAACGGATTGCAGC/FAM-
dT/GCGTATGGTGTGGCGAC/TAM/-5'          (SEQ ID NO.: 10)
```

(2) Similarly, Primer vPA1(ms1)F (5'-CATCCTGGTTT-GTGTTTTGCCTAAT-3'; SEQ ID NO.: 11) was allowed to anneal to PAPbttm to form a duplex as shown below as vSub(ms@-1):

```
5'-CATCCTGGTTTGTGTTTTGCCTAAT-3'      (SEQ ID NO.: 11)
   ||||||||||||||||||||||||.
3'-GTAGGACCAAACACAAAACGGATTGCAGC/FAM-
dT/GCGTATGGTGTGGCGAC/TAM/-5'          (SEQ ID NO.: 10)
```

(3) Similarly, Primer PA1F (5'-CATCCTGGTTTGT-GTTTTGCCTAA/ddC/-3'; SEQ ID NO.: 1) was allowed to anneal to PAPbttm to form a duplex as shown below as Sub(PM):

```
5'-CATCCTGGTTTGTGTTTTGCCTAA/ddC/-3' (SEQ ID NO.: 1)
   ||||||||||||||||||||||||
3'-GTAGGACCAAACACAAAACGGATTGCAGC/FAM-
dT/GCGTATGGTGTGGCGAC/TAM/-5'        (SEQ ID NO.: 10)
```

(4) Similarly, Primer PA1F was allowed to anneal to PAPbttm-T (5'-/TAM/CAGCGTGTGGTATGCG/FAM-dT/CGACTTTAGGCAAAACACAAACCAG-GATG-3'; SEQ ID NO.: 12) to form a duplex as shown below as Sub(ms@-1):

```
5'-CATCCTGGTTTGTGTTTTGCCTAA/ddC/-3' (SEQ ID NO.: 1)
   |||||||||||||||||||||||| .
3'-GTAGGACCAAACACAAAACGGATTGCAGC/FAM-
dT/GCGTATGGTGTGGCGAC/TAM/-5'        (SEQ ID NO.: 12)
```

The primers in vSub(PM) and vSub(ms@-1) are not blocked. The two substrates were used for regular reactions. The primers in Sub(PM) and Sub(ms@-1) are blocked. The two substrates were used for linear reactions that involve deblocking and extension referred as coupled reactions.

Each linear amplification assay contained 50 mM Tris, pH 8 (Teknova, Hollister, Ca), 2.5 mM MgCl$_2$ (ABI, Foster City, Calif.), 0.1% Tween 20 (Thermo Fisher, Rockford, Ill.), 0.25 mM total dNTP (ABI, Foster City, Calif.), 500 nM substrate, about 1 uM of ROX (Molecular Probes, Eugene, Oreg.), 150 µM tripolyphosphate (Cat #T5633, Sigma-Aldrich, St, Louis, Mo.) for triphosphate reactions or 30 µM pyrophosphate for PPi-reactions, and none of triphosphate or PPi for vanilla reactions, and 16.76 pg/µL 10A for vanilla reactions or 1.47 ng/µL 10A for triphosphate- or PPi-initiated reactions. The reaction time courses of triphosphate-initiated reactions with Sub(PM) and Sub(ms@-1) are shown in FIG. 9A.

Figures 9A, 9B:
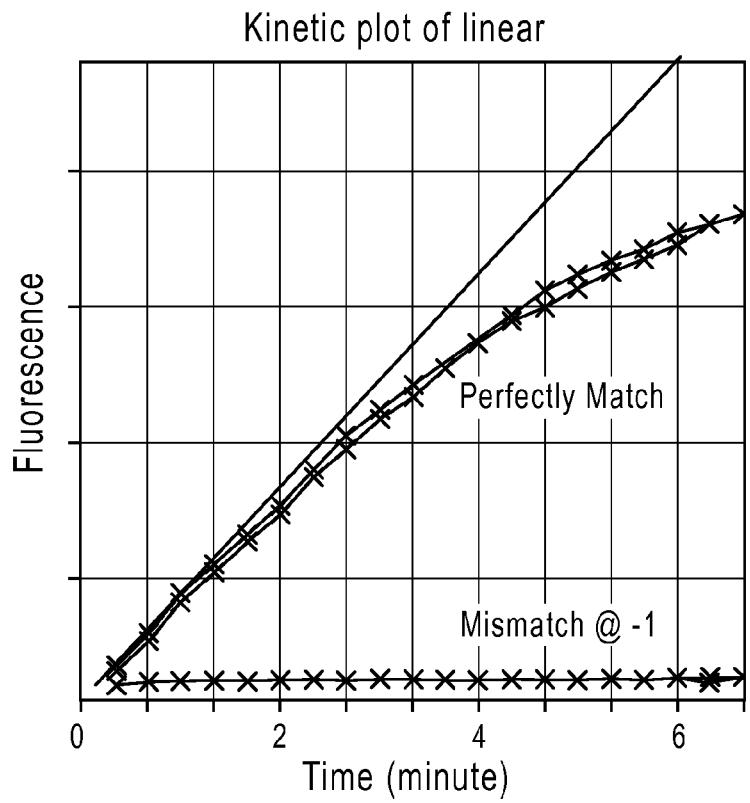
FIGS. 9A and 9B.

In FIG. 9B, the reaction rates relative to the rate obtained with their respective perfectly matched substrate are tabulated. For the vanilla reaction, the rate obtained using vSub(ms@-1) was 28% of the rate obtained using vSub (PM). In contrast, the rate obtained using Sub(ms@-1) was only 0.98% of the rate obtained using Sub(PM) for the coupled reaction where PPi was used to deblock the primer. The vast difference in reaction rate could explain the stringent reaction reported earlier.

Furthermore, the rate obtained using Sub(ms@-1) was 0.46% of the rate obtained using Sub(PM) when triphosphate was used to deblock the reaction. While the PPi reaction exhibited an error rate of 98 per 10,000 correct starts, triphosphate-catalyzed reactions exhibited an error rate of only 46 per 10,000 correct starts. Thus, triphosphate-initiated deblocking reactions unexpectedly exhibit improved stringency over PPi-initiated deblocking reactions, consistent with PCR results shown in Example 5 and Example 6. Therefore, triphosphate-catalyzed reactions are not due to the conversion of triphosphate to PPi.

Example 8

Deblocking and Extension with Triphosphate

Therminator III DNA polymerase is a 9° N$_m$ DNA polymerase variant with an enhanced ability to incorporate modified substrates such as dideoxynucleotides (Gardner, A F and Jack, W E, 1999, NAR 27:2545-2555; Gardner, A F and Jack, W E, 2002, NAR 30: 605-613). It belongs to the Pol B family. This example demonstrated that triphosphate-initiated deblocking was effective using Therminator III.

In the experiment, Primer PA16 (5'-GATCCTTTAGT-GCTGGACTGACC-3'; SEQ ID NO.: 67) was first allowed to anneal to PA16Fbottm (5'-/TAM/CAGCGTGTGGTAT-GCG/FAM-dT/CGACGGTCAGTCCAG-CACTAAAGGATC-3'; SEQ ID NO.: 13) to form a duplex as shown below as Sub(PA16F):

```
5'-GATCCTTTAGTGCTGGACTGAC/ddC/-3'(SEQ ID NO.: 67)
   |||||||||||||||||||||| .
3'-CTAGGAAATCACGACCTGACTGGCAGC/FAM-
dT/GCGTATGGTGTGGCGAC/TAM/-5'        (SEQ ID NO.: 13)
```

Figure 10:
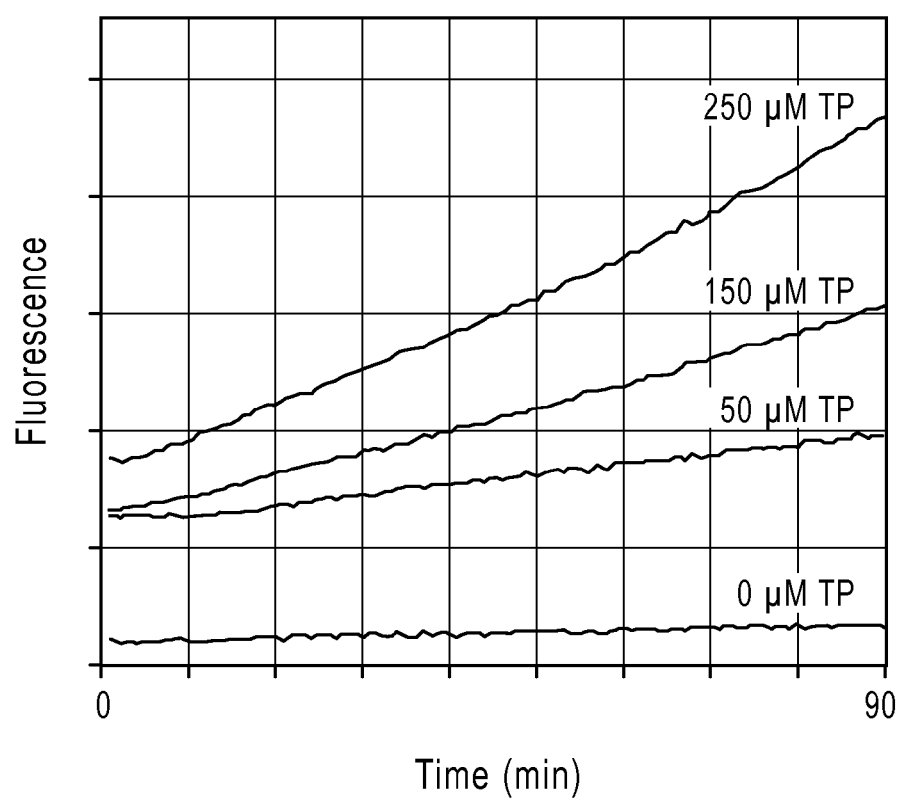
FIG. 10. Linear extension by Terminator III in the presence of various concentrations of TP FIG. 11. Deblocking and extension of a ddC-blocked primer by RQY using $Mn^{++}$ as the co-factor.

Then, the substrate at final concentration of 500 nM was allowed to react at 65° C. with Therminator III (final concentration at 0.027 unit/4) in 1× ThermoPol Buffer (provided by New England BioLabs) with added dNTP to final 0.25 mM and 0, 50, 150, or 250 µM of triphosphate. The reaction time courses are shown in FIG. 10. The fluorescent change rate accelerated as the concentration of triphosphate increased.

Example 9

Deblocking and Extension by RQY in the Presence of Triphosphate and Mn$^{2+}$

Figure 11:
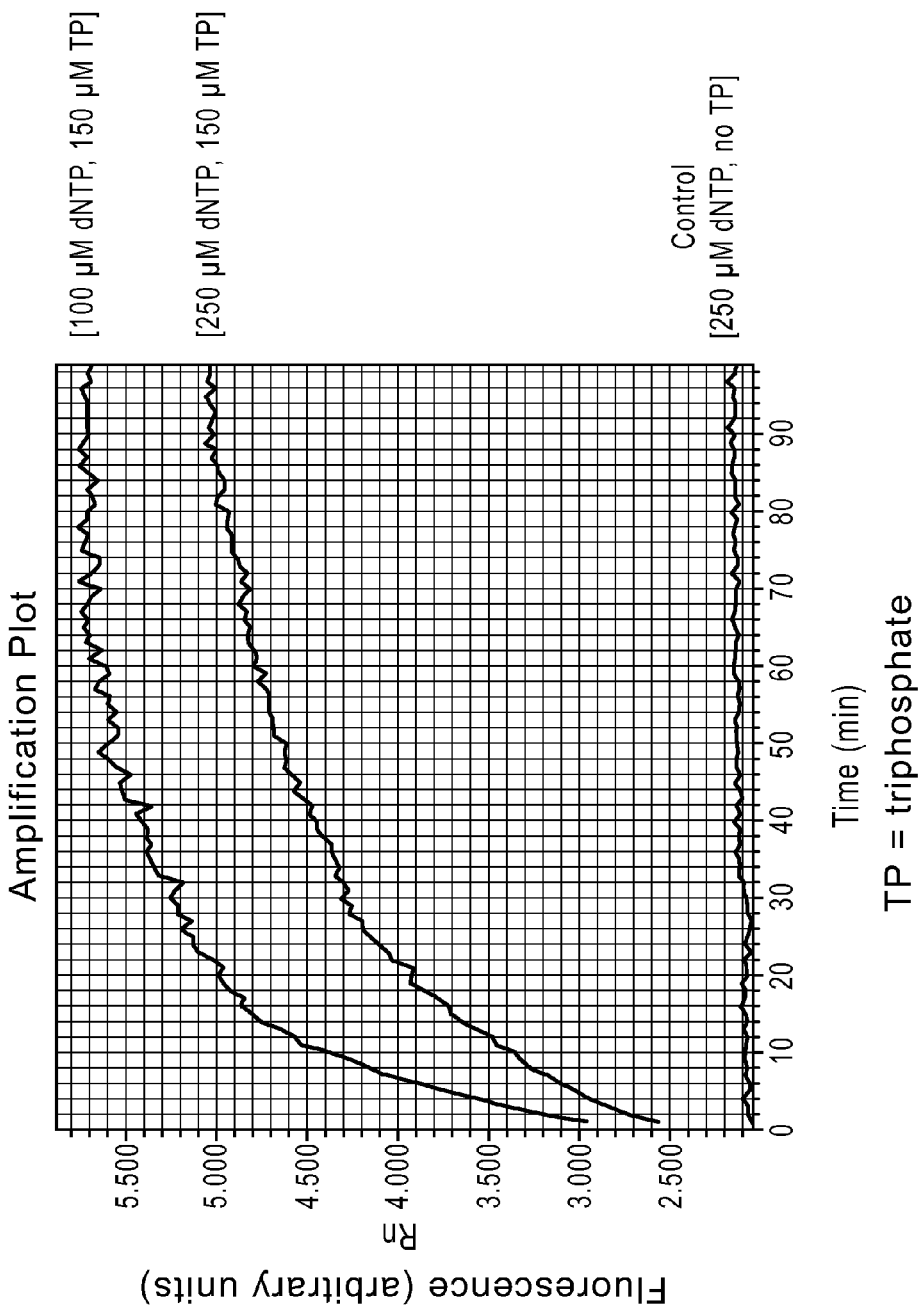

RQ1 is a thermostable DNA polymerase from *Thermus thermophilus* (U.S. Pat. No. 7,422,872, incorporated herein by reference in its entirety). It belongs to Pol A family. The Sub(PM) in Example 7 at final concentration of 500 nM was used in reactions that contained 50 mM Tris/HCl, pH8.0, 2.5 mM MnOAC$_2$, triphosphate and either 250 or 100 µM dNTPs and the RQY polymerase (a mutant of RQ1 including the substitution of phenylalanine 669 with tyrosine). The reaction time courses are shown in FIG. 11. It is clear that RQY is able to deblock ddC in the presence of triphosphate and Mn$^{2+}$, and extend the activated primer to generate fluorescence change. Without triphosphate, the deblocking was not effected.

Example 10

Tetraphosphate is an Effective Deblocking Reagent

Figure 12A:
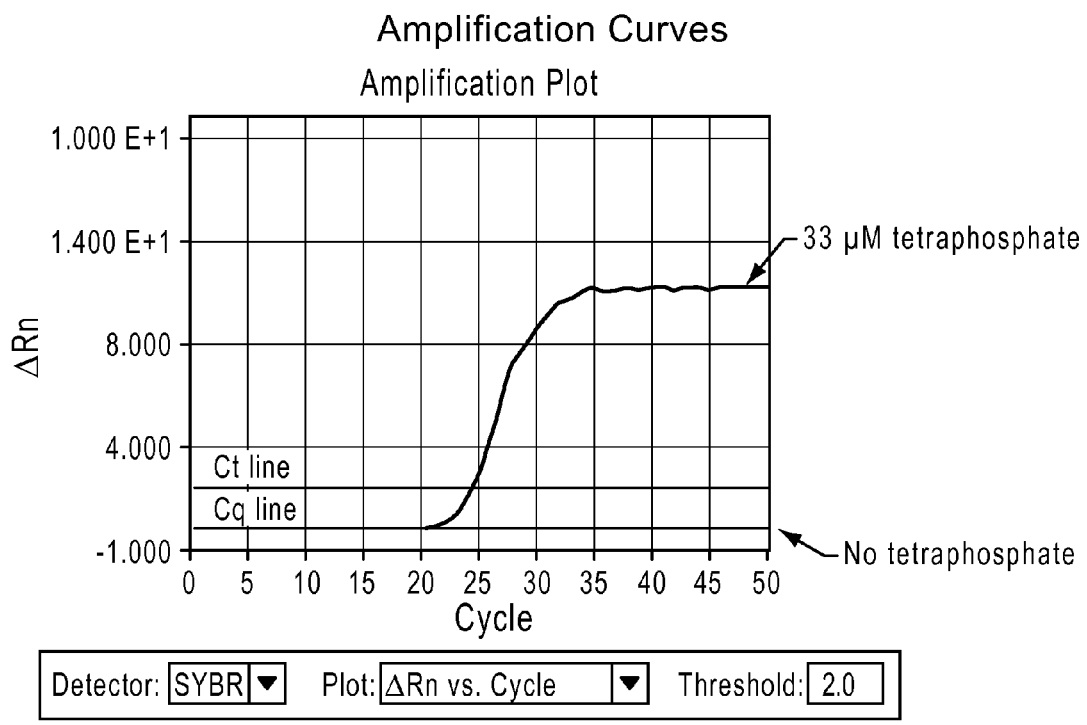
FIGS. 12A and 12B.
Figure 12B:
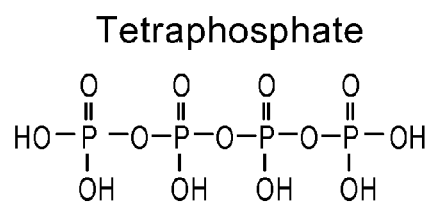

Tetraphosphate is a polyphosphate that follows the formula:

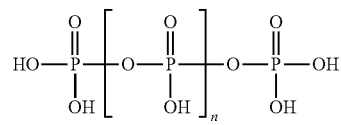

where n=2 (FIG. 12B). This example is to demonstrate that tetraphosphate at 33 µM is an effective deblocking agent and is useful in APP.

The 20 µl-reaction contained 50 mM Tris/HCl, pH8.5, 2. mM MgCl$_2$, 33 µM tetraphosphate, 1.5×SYBR Green, 31 µM dNTP, 15 mM (NH$_3$)$_2$SO$_4$, Tween 0.1%, 2 pg/µl 10A per 20 µl reaction, 500 nM PA-1F (5'-CATCCTGGTTTGT-GTTTTGCCTAA(ddC)-3'; SEQ ID NO.: 1), 500 nM PA-1R (5'-GGGAGAAAAAAGCCAACCTTAATG(ddC)-3' SEQ ID NO.: 2), and a total of 20 ng of human DNA. The negative control reaction contained no tetraphosphate. The tetraphosphate-catalyzed reactions were performed using an ABI 7900 Sequence Detection System with the following temperature profile: 50 cycles of 95° C., 3 seconds, then 65° C., 60 seconds. The result is shown in FIG. 12A. The reaction with tetraphosphate exhibited a positive amplification curve, while without tetraphosphate, the reaction did not take off in fifty cycles.

Example 11

APP Using Imidodiphosphate (IDP)

Figure 13A:
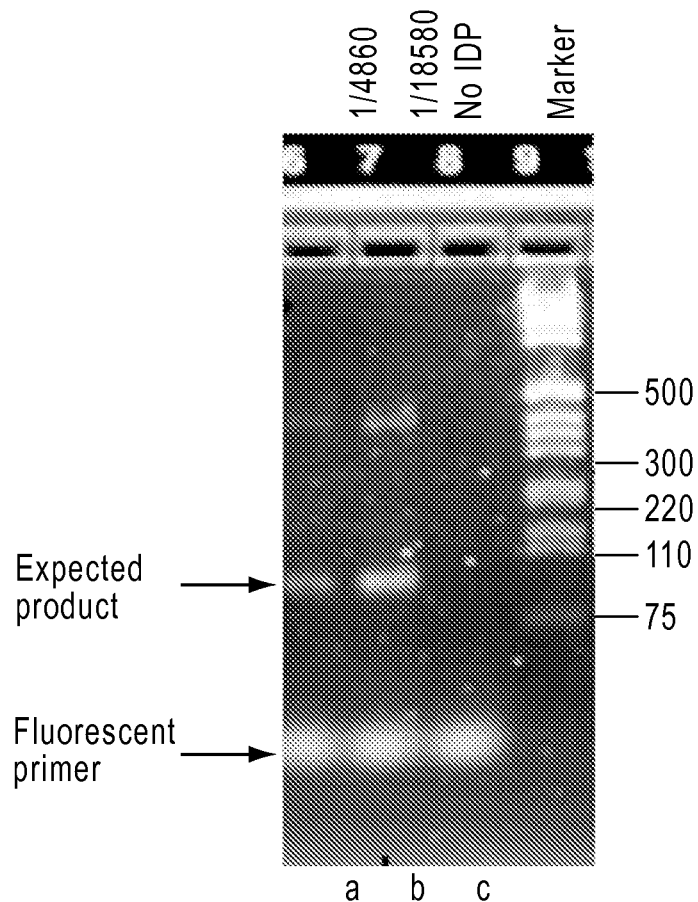
FIGS. 13A and 13B.
Figure 13B:
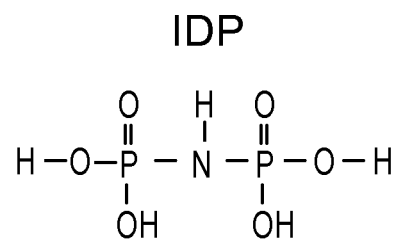

IDP (imidodiphosphate, Sigma-Aldrich Cat #, CAS #26039-10-1; FIG. 13B) has a molecular formula showing below:

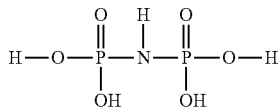

This example demonstrates that IDP is useful in APP.

The 20 µl-reaction contained 50 mM Tris/HCl, pH8.25, 1.5 mM MgCl$_2$, 62.5 µM dNTP, 0.1% Tween 20, 5 unit of TaqFS, 500 nM SBTaqGn1598Fmu, 500 nM 1699LR (SEQ ID NO.: 9), about 1 million copies of p540D with insert that has SEQ ID NO.: 7 and with (a) final 1/4860 dilution of saturated IDP solution, or (b) 1/18580 dilution of saturated IDP solution or (c) no IDP.

SBTaqGn1598Fmu has the sequence as 5'-(BHQ)-TG-CAATACCGTGAGC(FAM-dT)GACC(ddC) (SEQ ID NO.: 14). The IDP-catalyzed reactions were performed using an ABI 7900 Sequence Detection System with the following temperature profile: 50 cycles of 95° C., 3 seconds, then 65° C., 120 seconds. The PCR products were run on an Ethidium Bromide Agarose gel (1%) as shown in FIG. 13A. Only reactions with IDP generated the specific product while reaction with no IDP generated no products.

Example 12

Pentaphosphate and Hexaphosphate are Effective Deblocking Reagents

Pentaphosphate is a polyphosphate that follows the formula:

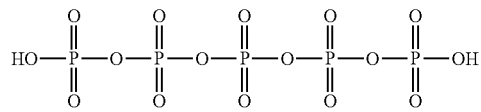

This example is to demonstrate that pentaphosphate is an effective deblocking agent and is useful in carrying out an APP reaction.

The 20 µl-reaction contains 50 mM Tris/HCl, pH8.5, 2. mM MgCl$_2$, 33 µM penta- or hexa-phosphate, 1.5×SYBR Green, 31 µM dNTP, 15 mM (NH$_3$)$_2$SO$_4$, Tween 0.1%, 2 pg/µl 10A per 20 µl reaction, 500 nM PA-1F (5'-CATCCTG-GTTTGTGTTTTGCCTAA(ddC)-3'; SEQ ID NO.: 1), 500 nM PA-1R (5'-GGGAGAAAAAAGCCAACCTTAATG (ddC)-3' SEQ ID NO.: 2), and a total of 20 ng of human DNA. The negative control reaction contains no pentaphosphate. The pentaphosphate-catalyzed reactions are performed using an ABI 7900 Sequence Detection System with the following temperature profile: 50 cycles of 95° C., 3 seconds, then 65° C., 60 seconds. The reaction is expected to show positive amplification curve.

Example 13

Preventing Primer-Dimer Formation

PCR is prone to form primer dimers when 3' regions of the primers are complementary to or partially-complementary to each other. This example serves to demonstrate that APP is an effective tool to reduce primer dimer formation in PCR even when substantial complementarities exist between primers.

Table I lists primers and their sequences used in this example to evaluate the potentials to form primer dimers. Regular primers vPA17PD4F (SEQ ID NO.: 16), vPA17PD6F (SEQ ID NO.: 17), and vPA17PD9F (SEQ ID NO.: 18) are synthesized so that they make 4, 6, and 9 base pairs with vPA17R (SEQ ID NO.: 15) at 3' ends. PA17PD4F, PA17PD6F, and PA17PD9F, and PA17R are the APP counterparts with dideoxy endings. The underlines in Table I indicate the complementary region to the corresponding reverse primers.

TABLE I

Primer Sequences and Ct's in Primer-dimer Formation Assays

| Primer | Primer Sequence | SEQ ID Number | Ct in PCR* |
|---|---|---|---|
| vPA17R | CCATAACCAGACTCAGCAGAGAAC | SEQ ID NO.: 15 | — |
| vPA17PD4F | GCTCCAGACAGAAACACC<u>GTTC</u> | SEQ ID NO.: 16 | 33 |
| vPA17PD6F | GCTCCAGACAGAAACA<u>GTTCTC</u> | SEQ ID NO.: 17 | 19 |
| vPA17PD9F | GCTCCAGACAGAA<u>GTTCTCTGC</u> | SEQ ID NO.: 18 | 2 |
| PA17R | CCATAACCAGACTCAGCAGAGAA/ddC/ | SEQ ID NO.: 15 | — |
| PA17PD4F | GCTCCAGACAGAAACACC<u>GTT/ddC/</u> | SEQ ID NO.: 16 | 40 |

TABLE I-continued

Primer Sequences and Ct's in Primer-dimer Formation Assays

| Primer | Primer Sequence | SEQ ID Number | Ct in PCR* |
|---|---|---|---|
| PA17PD6F | GCTCCAGACAGAAACAGTTCT/ddC/ | SEQ ID NO.: 17 | 34 |
| PA17PD9F | GCTCCAGACAGAAGTTCTCTG/ddC/ | SEQ ID NO.: 18 | 29 |

*— Ct in PCR when paired with the corresponding forward primer

Figure 14:
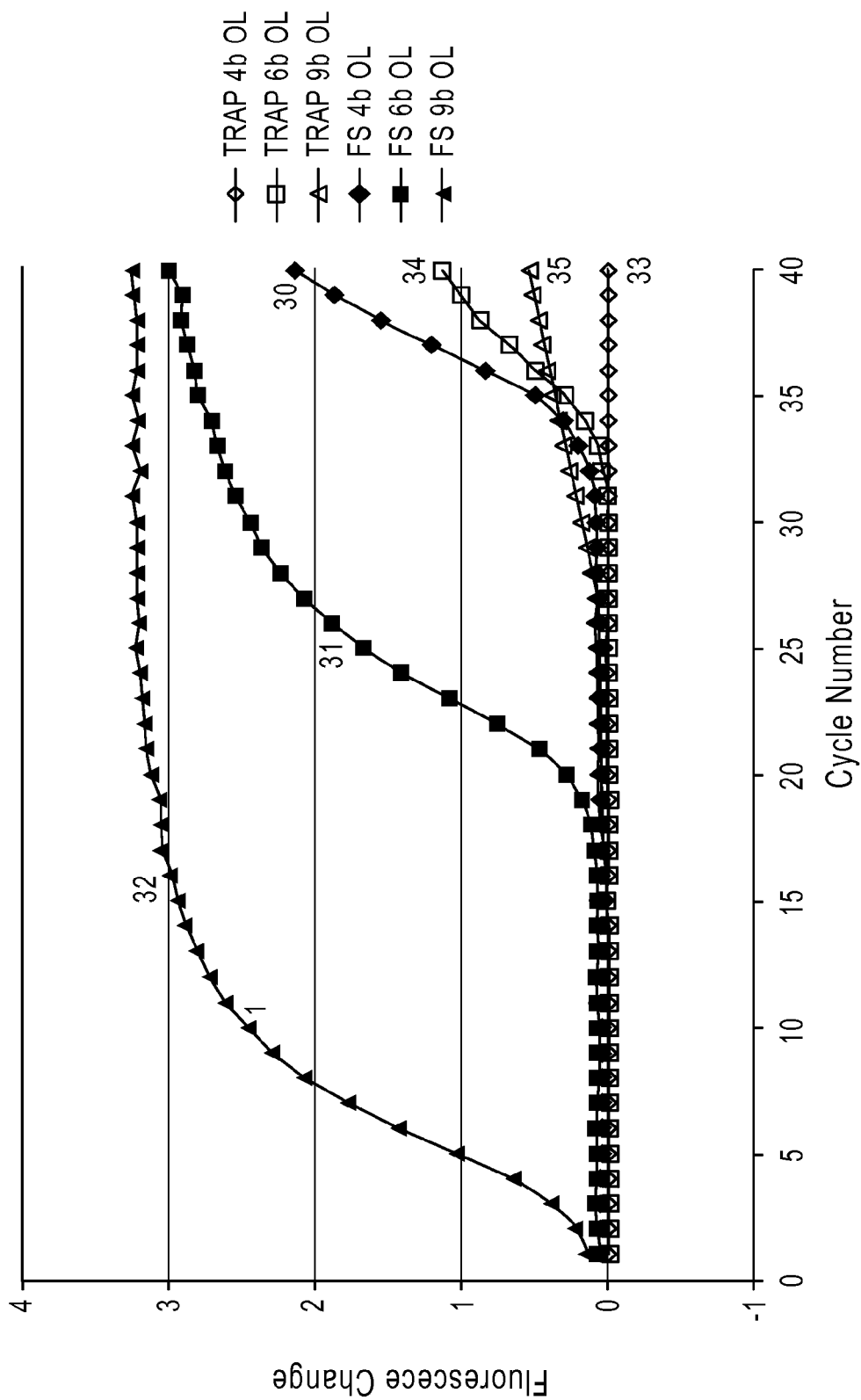
FIG. 14. Amplification curves between primers that has 4-(diamond), 6-(square), or 9-(triangle) bases overlaps in regular PCR (filled) and in APP PCR (open).

The regular PCR reaction of 20 μL contains 1× Fast SYBR Green Master Mix (Life Technologies, ABI Cat #4385612), and 500 nM of forward and reverse primers, with each primer pair having 4, 6 and 9 bases overlaps respectively. Assays were performed using an ABI 7900 Sequence Detection System with the following temperature profile: 40 cycles of 95° C., 3 seconds, then 65° C., 60 seconds. The reaction profiles are shown in FIG. 14. Traces 30, 31, and 32 are the regular reactions of 4, 6, and 9 base-pair overlaps.

The APP reactions of 20 μL contains 50 mM Tris/HCl, pH8.5, 2.5 mM MgCl$_2$, 350 μM triphosphate, 0.5×SYBR Green, 31 μM dNTP, 15 mM (NH$_3$)$_2$SO$_4$, Tween 0.1%, 6 ng/μl 10A, 500 nM each of forward and reverse primers of 4, 6 and 9 bases overlaps respectively. Assays were performed using an ABI 7900 Sequence Detection System with the following temperature profile: 40 cycles of 95° C., 3 seconds, then 65° C., 60 seconds. The reaction profiles are shown in FIG. 14. Traces 33, 34, and 35 are APP reactions by APP primers of 4, 6, and 9 base-pairs overlaps.

The Ct's of regular reaction and APP reaction are 33 and 40 respectively for 4-base overlapping reactions, showing a 128 fold decrease in potential of primer dimer formation in the APP reaction (assuming 2 fold decrease for every 1 cycle delay). The Ct's of regular reaction and APP reaction are 19 and 34 respectively for 6-base overlapping reactions, showing a near 33 thousands fold decrease in potential of primer dimer formation in the APP reaction. The Ct's of regular reaction and APP reaction are 2 and 29 respectively for 9-base overlapping reactions, showing an over 130 million fold decrease in potential of primer dimer formation in the APP reaction.

Example 14

Primer-Dimer Formation in Multiplex Assays

Figure 15:
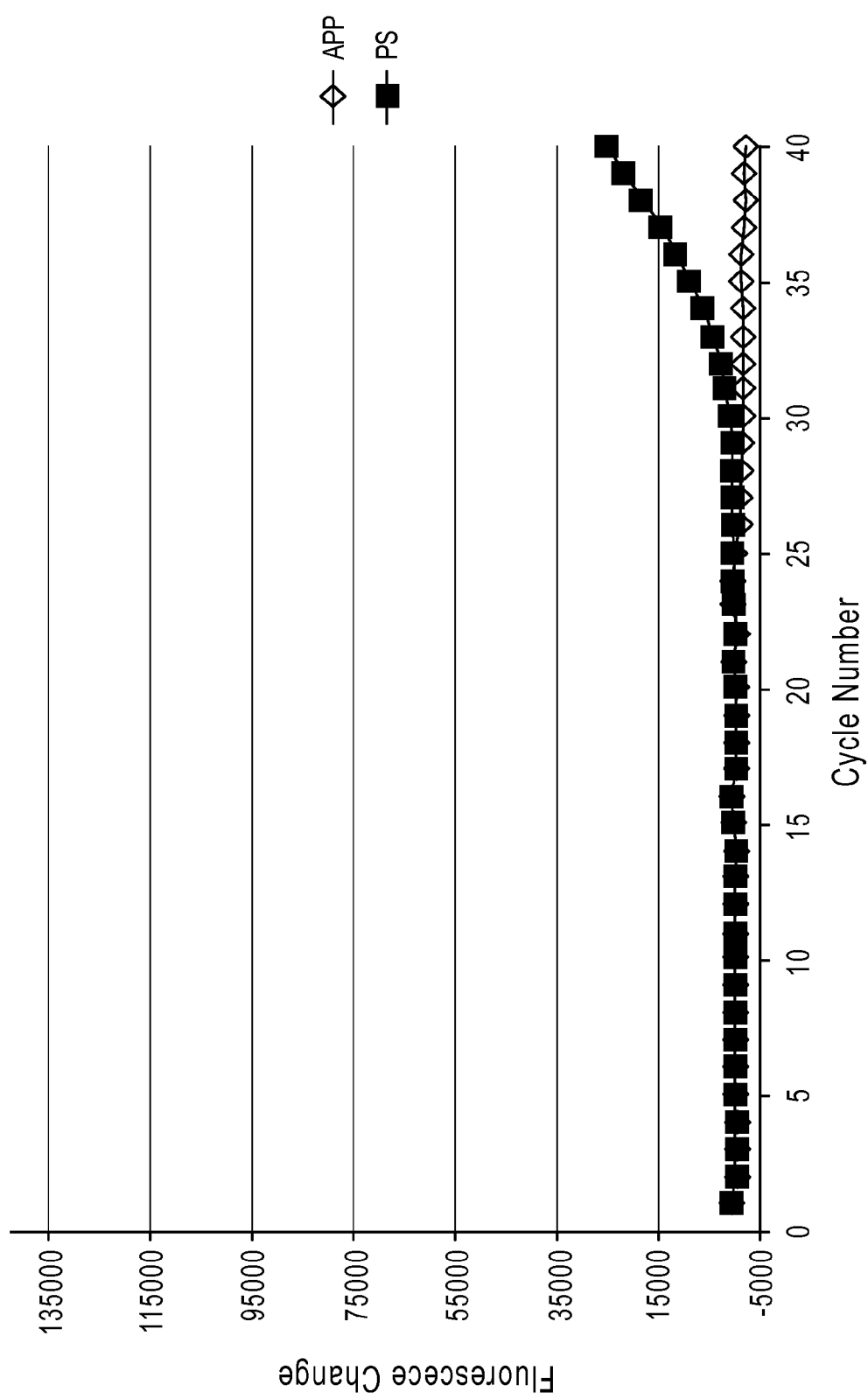
FIG. 15. Amplification curves of by 48 primers alone in regular PCR (filled), and APP PCR (open).

In multiplex reactions, the chance to form primer dimer increases as the number of primers increases. A regular multiplex PCR reaction of 20 μL, cycling between 95° C. for 5 second and 65° C. for 1 minute, contained 1× Power SYBR Green Master Mix (Life Technologies, ABI Cat #4368706) and 104 nM each of the primers listed in Table II, nonspecific signals came out at cycle of 31 (Trace 36, FIG. 15). When the primer sequences were kept the same but the last bases were changed to terminators (Table III), and the amplification was carried in APP multiplex reaction (20 uL of 50 mM Tris/HCl, pH8.5, 2.5 mM MgCl$_2$, 300 μM triphosphate, 0.5×SYBR Green, 31 μM dNTP, 15 mM (NH$_3$)$_2$SO$_4$, Tween 0.1%, 6 ng/μl 10A), the non-specific reaction did not show up in 40 cycles (Trace 37, FIG. 15).

TABLE II

Primer Pools for regular and APP reactions

| Primer Sequences | SEQ ID NO. |
|---|---|
| CATCCTGGTTTGTGTTTTGCCTAAC | 19 |
| GACAATACTGTTCCAATTTGGCTCATC | 20 |
| GCTCCAGTTGTATCATCCCCTTTTC | 21 |
| CACAAAGACACGAAGAACATCATTGAC | 22 |
| GGGATGGCTCTATGGACAAAAAGAC | 23 |
| TGCCATGGTGCTTCATACAAGTATC | 24 |
| CCCGGTTAAATACCATGAGATTCTAAGC | 25 |
| GGAGCAAGCTTGAAGGAGTTAGAATC | 26 |
| CCATCAGGGAAGACTATCCTCAAAC | 27 |
| GCATAGCAGTCCCCAAGAATGAC | 28 |
| CTCGCCATCCCCACCATAC | 29 |
| CCTCTTCATCCTCACCCTTGC | 30 |
| CCTGCCCTTCAGAACCTAACAC | 31 |
| TCAGCACACCTATCGGAAAGC | 32 |
| GCGGATGCCTCCTTTGC | 33 |
| GATCCTTTAGTGCTGGACTGACC | 34 |
| GCTCCAGACAGAAACACCGTAC | 35 |
| ATCCTTGGTGGGACTGAACAC | 36 |
| CAGAGAGCGCCTCCTATTCTAC | 37 |
| GGAGAGAGACCTGGGAAAAGTC | 38 |
| AAGCGCTATGCAGAGAAGTACTC | 39 |
| GACACGTGCTTGAGGAAACAC | 40 |
| GCAGACTAGGCTGCATTCACTC | 41 |
| AGAGCTGCGTGGACACTAC | 42 |
| GGGAGAAAAAGCCAACCTTAATGC | 43 |
| ATTAAACGATTACCCTGAGGATGATATGC | 44 |
| GGTGCGTTTTCTTCCCATATTCC | 45 |
| TCTTTTATATCCCCTTCGTCTGCAAAC | 46 |
| GTTAAATGGTGGTGGTGCATTCAC | 47 |
| GCGGTCCAAGGAATTTTGCTAAC | 48 |
| CAAACACCCCTTATTCCAGTCAAAC | 49 |
| CCACTTTTTCCCAACCCCAAAATTC | 50 |
| GCAGACCCAAGTTTCCTTTCTCC | 51 |

TABLE II-continued

Primer Pools for reqular and APP reactions

| Primer Sequences | SEQ ID NO. |
|---|---|
| CGGTTCCCACGAAAAGCAAC | 52 |
| CACTGAGCAACACAATTGGACTTTC | 53 |
| CCTGGCTTATCACCTTGGACTTC | 54 |
| TGTCTTGGGTGGGTTTCTCTTAAC | 55 |
| CCCAGACTCCTCCCTTGTTTC | 56 |
| ACCTCAGCCATTGAACTCACTTC | 57 |
| CTGCTCTACTGGTTTCCCTAGATTC | 58 |
| CCATAACCAGACTCAGCAGAGAAC | 59 |
| CAAACCCACCGCAGTAACTTAC | 60 |
| GCCTGCCCAGGACTTACTC | 61 |
| AGGTATGTGGCTGCTGTCTTC | 62 |
| AAGGAGGCGTCGCTGTAC | 63 |
| GCAGCCAGTCAACTCTGAAC | 64 |
| ACAGTCACCCTGCACACTTAC | 65 |
| CCCCGGGTGCGAAGTC | 66 |

Example 15

Digital PCR Using APP

Digital PCR (dPCR) is a refinement of conventional polymerase chain reaction methods that can be used to directly quantify and clonally amplify nucleic acids. With dPCR, a sample is partitioned so that individual nucleic acid molecules within the sample are localized and concentrated within many separate regions. The partitioning of the sample allows one to count the molecules by estimating according to Poisson distribution. As a result, each part will contain "0" or "1" molecules, or a negative or positive reaction, respectively. After PCR amplification, nucleic acids may be quantified by counting the regions that contain PCR end-product, positive reactions. "The partitioning of the sample" can be accomplished in individual wells, such as wells in a plate, wells in a card, or micelles in an emulsion. Partition can also be done in space without real physical barrier, such as in a bridge PCR, "polony", etc.

Figure 16A:
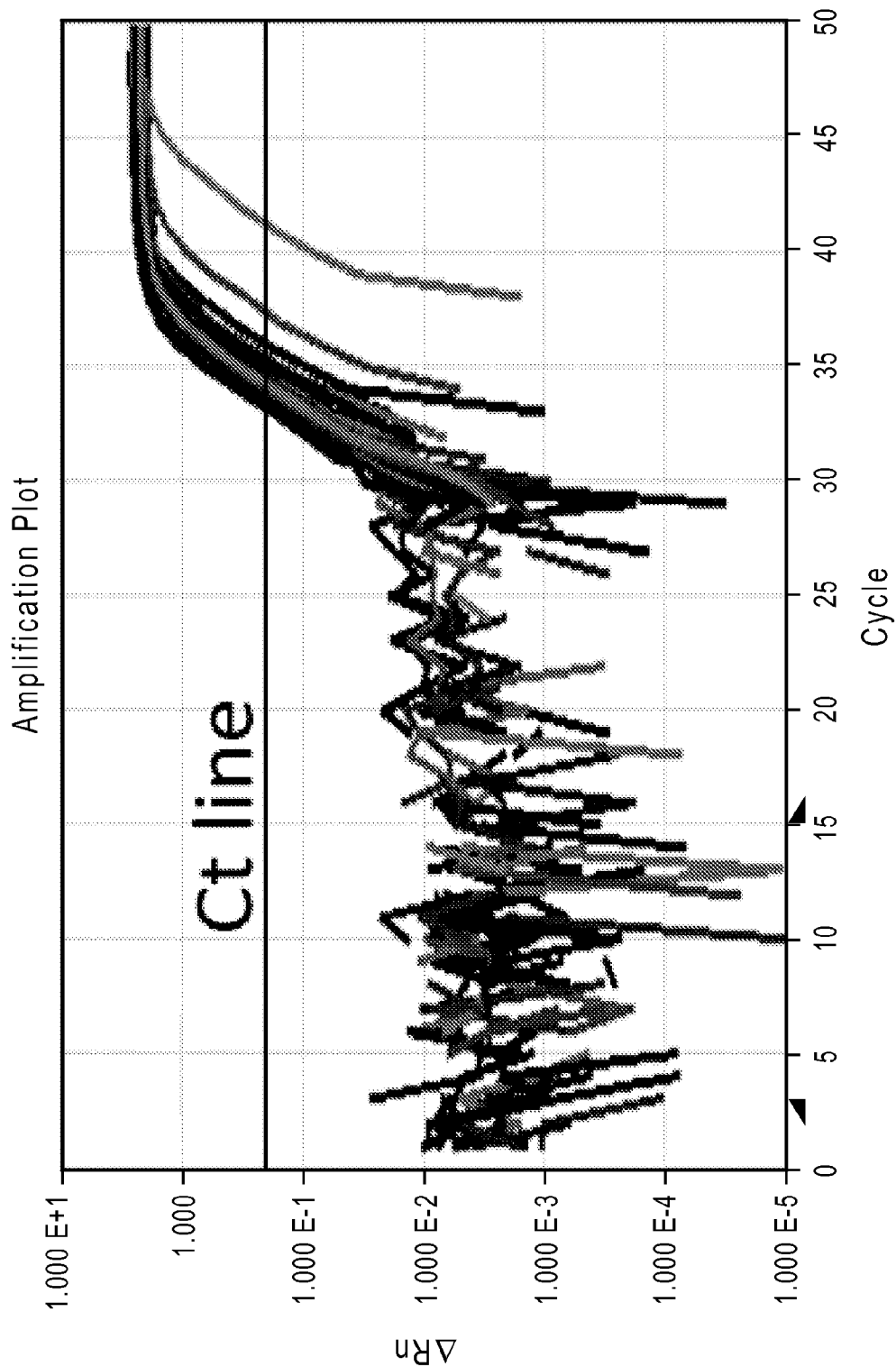
FIGS. 16A, 16B, 16C and 16D.
Figure 16B:
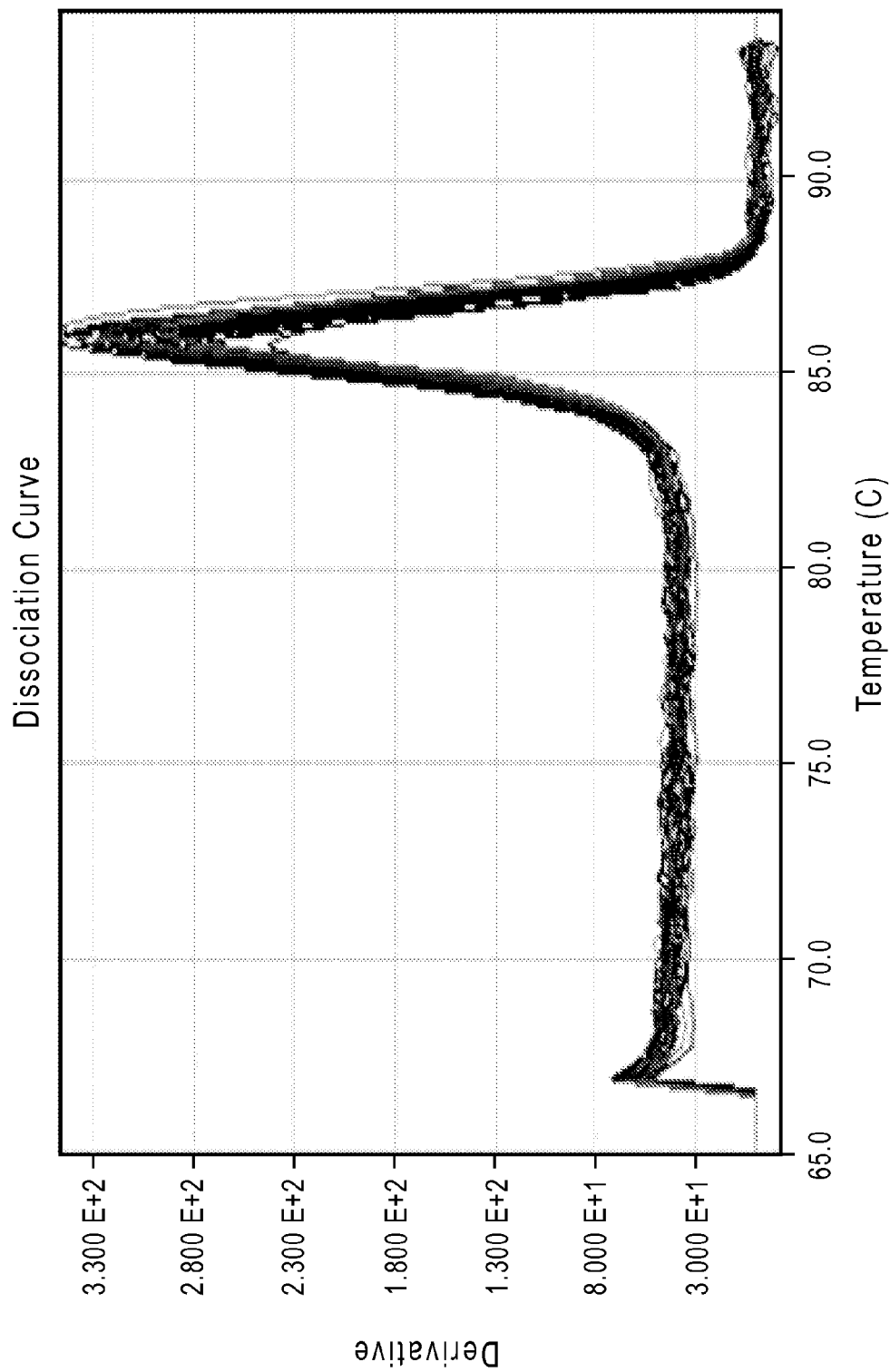
Figure 16C:
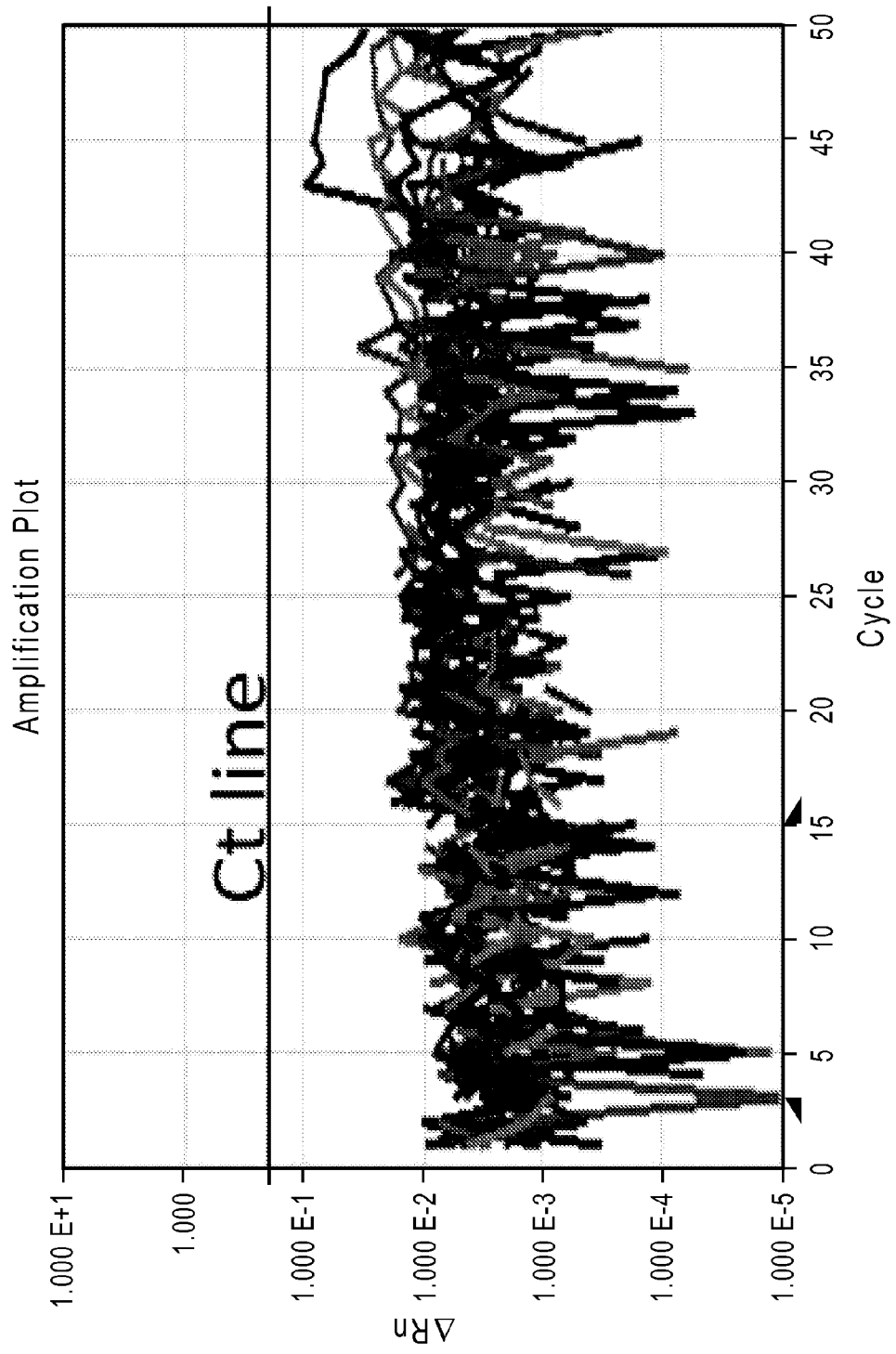
Figure 16D:
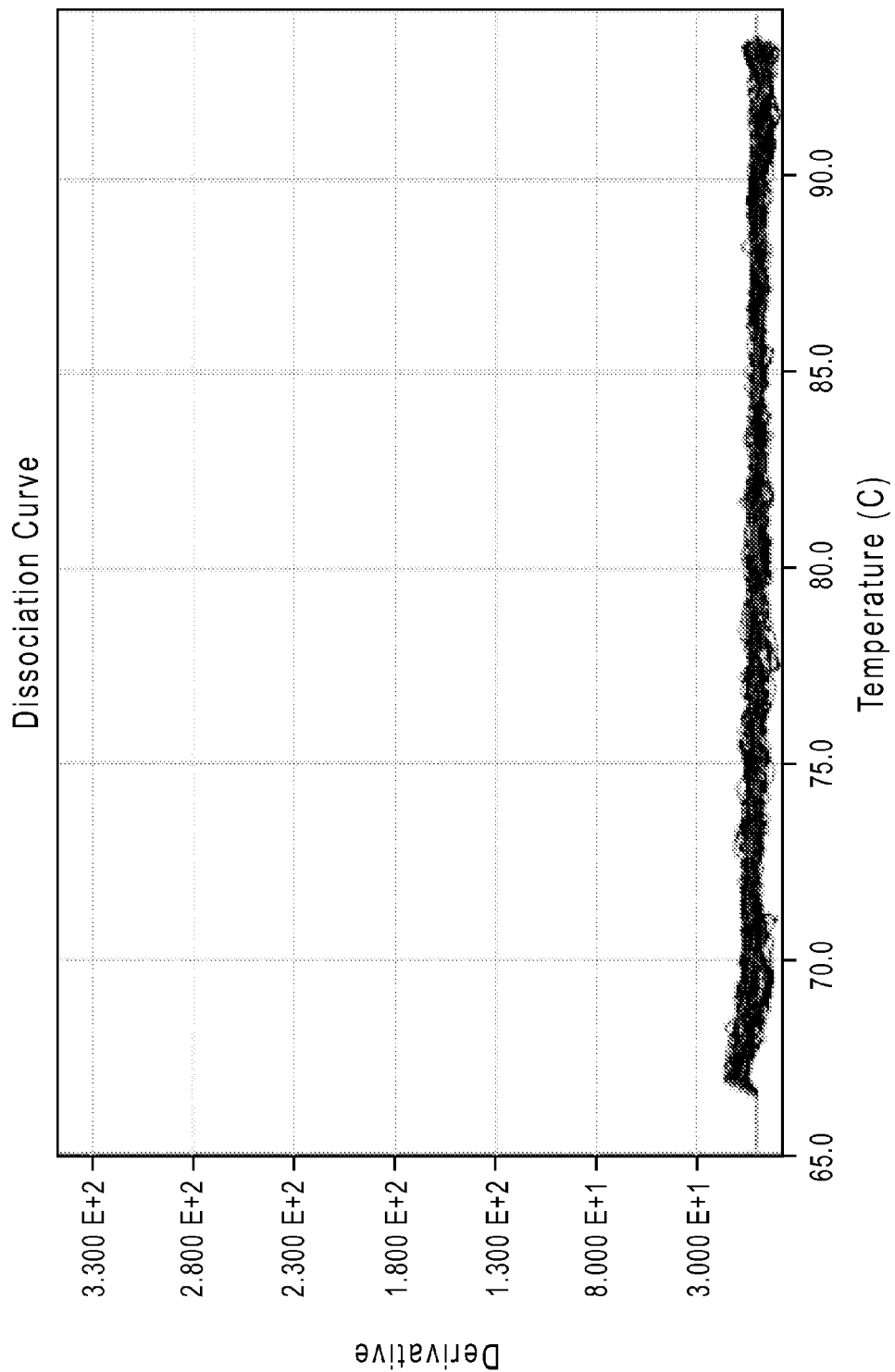

Conventionally, dPCR is widely monitored by TAQMAN detection. However, TAQMAN detection involves expensive probes that impede its wider application. This example demonstrates that APP, a cheaper approach, may be ideal for this application and may be superior to regular dye-based assay.

of 10 μL containing 50 mM Tris/HCl, pH8.5, 1.5 mM MgCl$_2$, 350 μM tetraphosphate, 0.5×SYBR Green, 31 μM dNTP, 15 mM (NH$_3$)$_2$SO$_4$, Tween 0.1%, 6 ng/μl 10A, 500 nM PA14F and PA14R, 1.5 ng of human DNA. Each reaction was cycled 50 times between 95° C. for 5 second and 65° C. for 1 minute. Of the 96 reactions, thirty-four (34) showed growth curves (FIG. 16A) and melting curves of Tm=86° C. (FIG. 16B). By definition, these are positive reactions. The rest sixty-two (62) are negatives, exhibiting neither growth curves (FIG. 16C), nor melting curves (FIG. 16D).

Figure 17A:
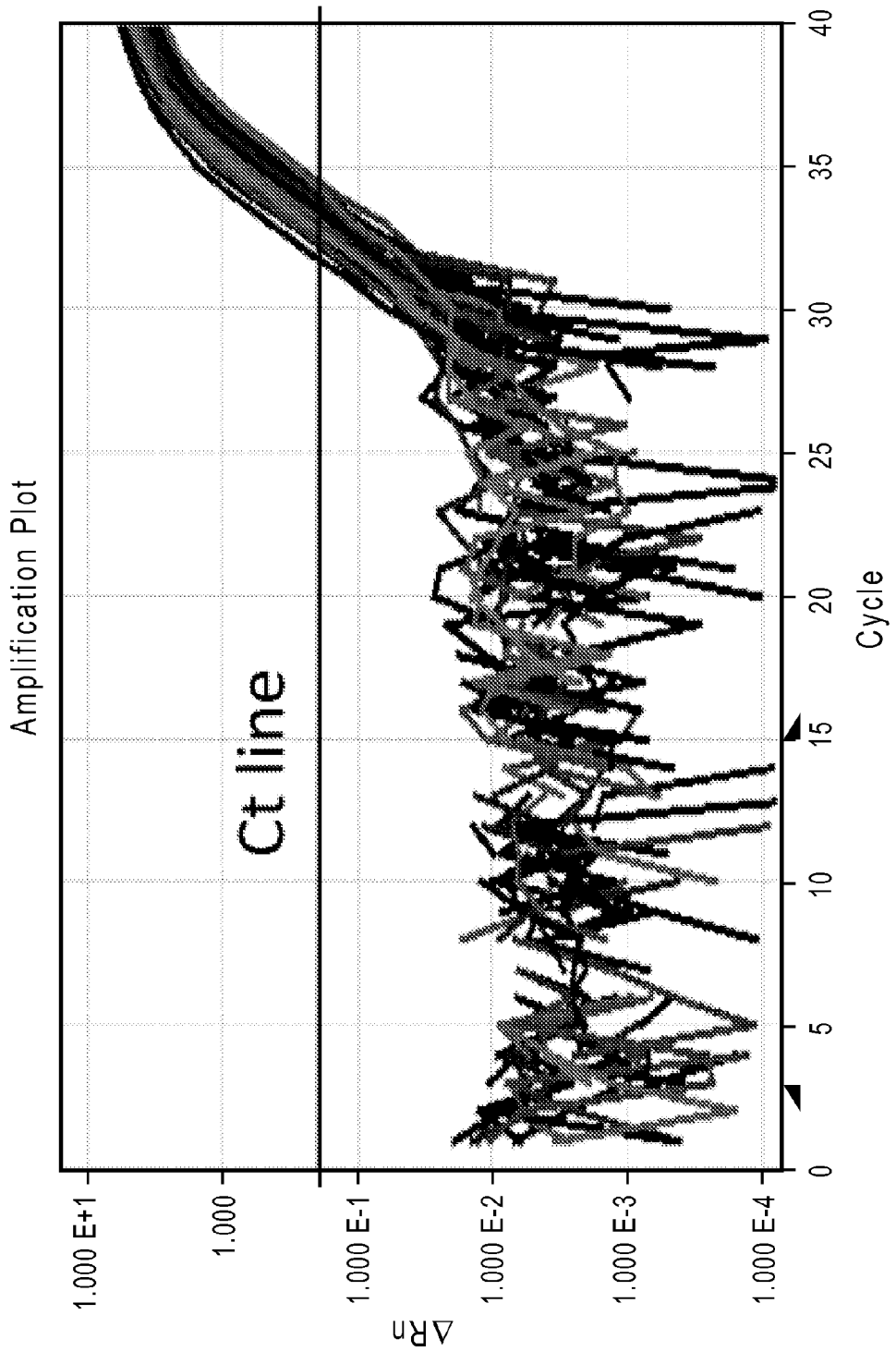
FIGS. 17A, 17B, 17C and 17D.

When dPCR was conducted using regular dye-based PCR technologies, to figure out positive from negatives were not straight forward. Specifically, regular dye-based dPCR was conducted in 96 partitions with each partition of 10 μL containing 1×SYBR GreenER qPCR Supermix (Life Technologies Cat #11760-500), 500 nM PA14F, 500 nMPA14R, and 1.5 ng of human DNA, in 50 cycles between 95° C. for 5 second and 65° C. for 1 minute. All 96 partitions showed growth curves (FIGS. 17A and 17C). Not one reaction well showed a single melting curve peak at 86° C., as the case in FIG. 16B. Instead, thirty nine (39) reaction wells have a peak at about 86° C. in addition to other peaks indicating additional non-specific amplification products. The other fifty seven (57) reaction wells also exhibited multiple peaks other than 86° C. The group of thirty nine was assigned as positives, while the group of fifty seven was assigned as negatives. It is easier to discern the positives from negatives and bears higher confidence using APP-dPCR compared to regular PCR.

TABLE IV

Primer Sequences Used in Digital PCR

| Primer Name | Primer Sequence | SEQ ID Number |
|---|---|---|
| vPA14F | TCAGCACACCTATCGGAAAGC | SEQ ID NO.: 68 |
| vPA14R | CCCAGACTCCTCCCTTGTTTC | SEQ ID NO.: 69 |
| PA14F | TCAGCACACCTATCGGAAAG/ddC/ | SEQ ID NO.: 68 |
| PA14R | CCCAGACTCCTCCCTTGTTT/ddC/ | SEQ ID NO.: 69 |

Figure 18B:
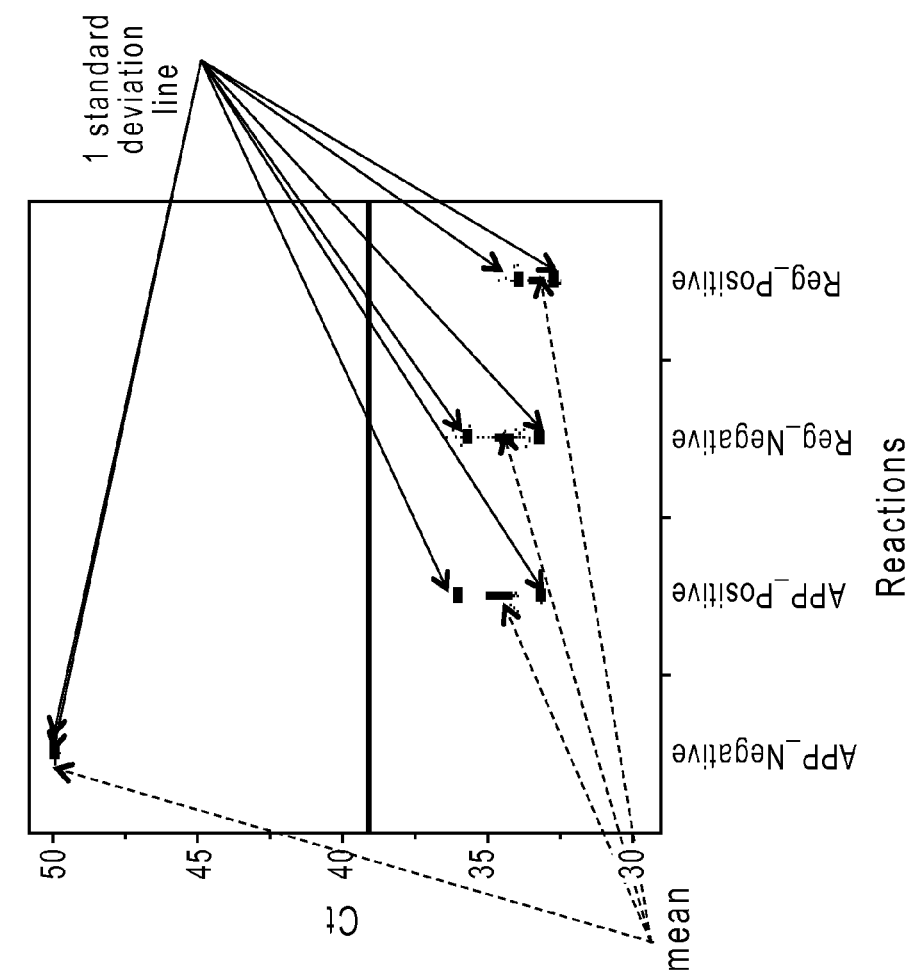
FIGS. 18A and 18B.
Figure 18A:
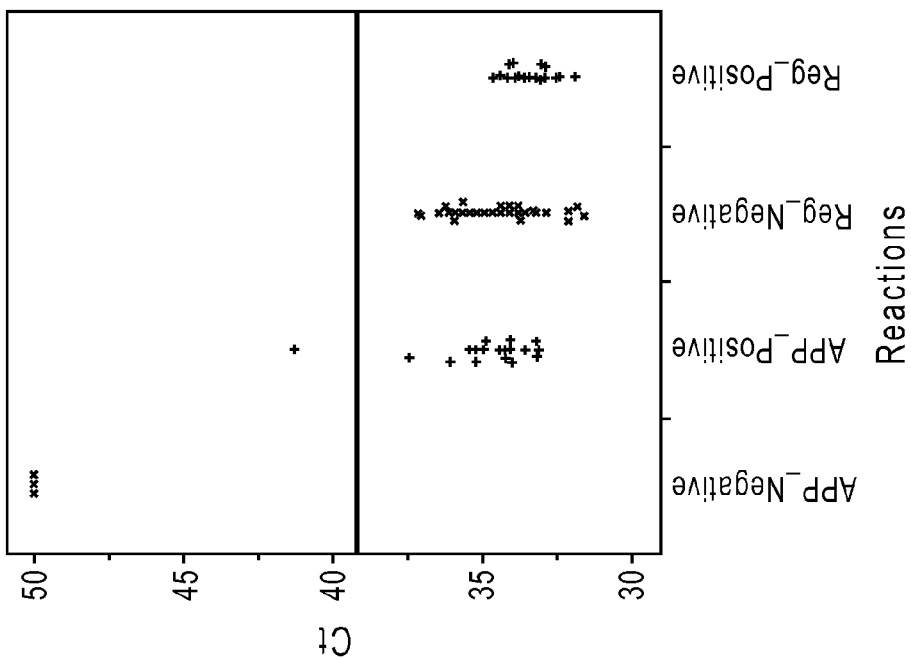

The distribution of Ct of negatives of APP, positives of APP, negatives of regular reaction and positives of regular reaction are plotted in FIG. 18A using JMP software. The same data was plotted in FIG. 18B to indicate the mean and 1× standard deviation. It is clear that in dPCR-APP, the positives are well separated from the negatives based on Ct, while in dPCR-regular, the positives cannot be separated from the negatives based on Ct, demonstrating the utility and the superiority of APP.

Figure 17B:
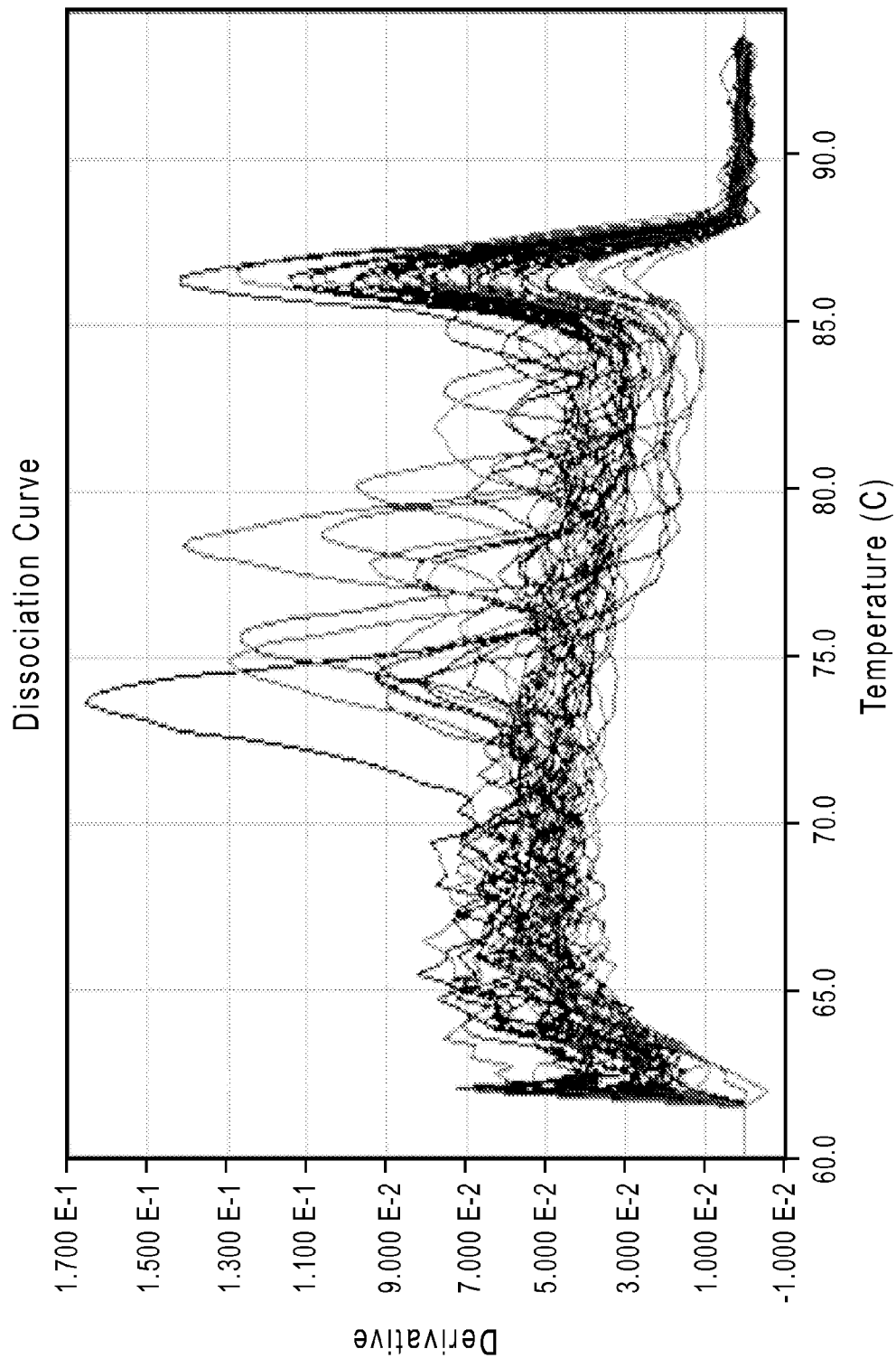
Figure 17C:
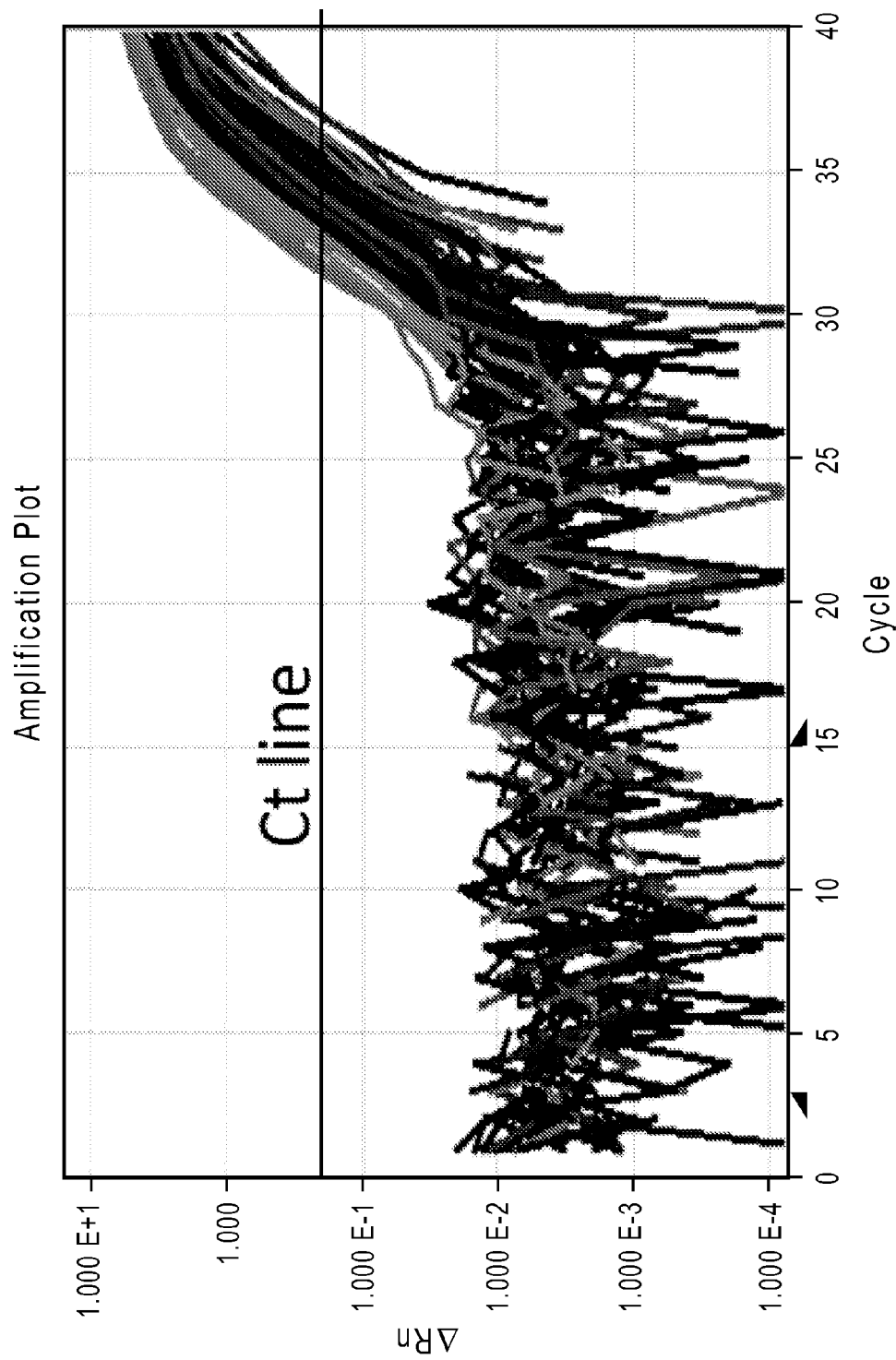
Figure 17D:
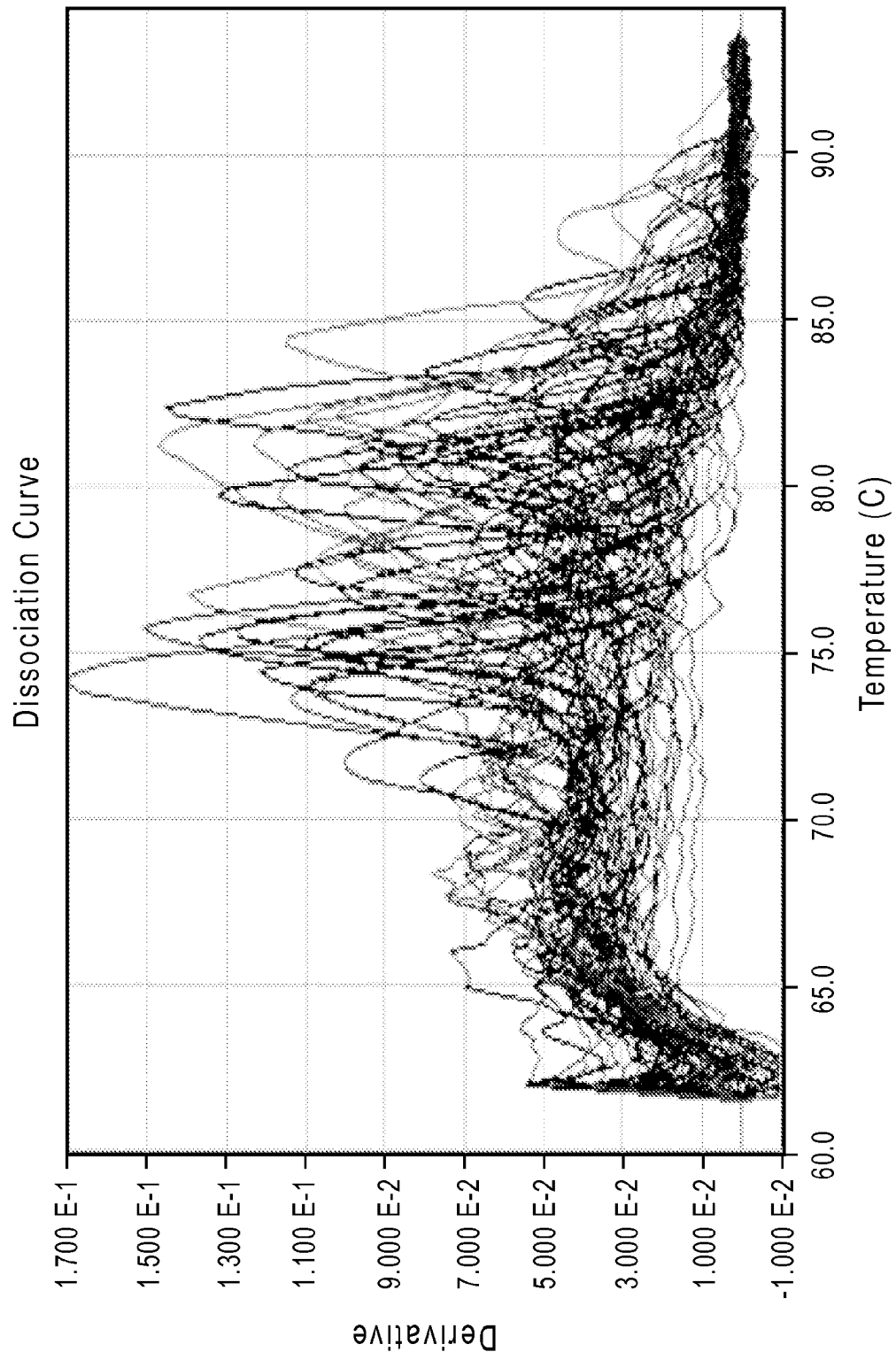

The melting curves between FIG. 16B and FIG. 17B suggest that APP would generate much cleaner products in clonally amplify nucleic acids.

All references cited within this disclosure are hereby incorporated by reference in their entirety. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for amplifying a target nucleic acid by an activation by polyphosphorolysis (APP) reaction comprising the steps of:

(a) annealing to a template strand of the target nucleic acid a complementary activatable oligonucleotide P* having a non-extendable nucleotide at its 3' terminus and having no mismatched nucleotides at or near its 3' terminus, so that the terminal nucleotide is hybridized to the template strand when the oligonucleotide P* is annealed, (b) polyphosphorolyzing the resulting duplex with:
  1) one or more polyphosphorolyzing agents selected from the group consisting of a compound of the general formula I:

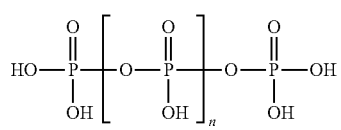

wherein n is selected from the group consisting of 1, 2, 3, 4, 5, 6, 7, 8, 9, and 10;

a compound of general formula II:

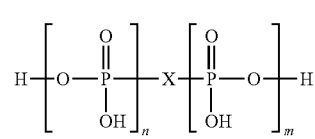

wherein n and/or m are selected from the group consisting of 0, 1, 2, 3, 4, 5, 6, 7, 8, 9, and 10, with the proviso that n and m cannot both be 0, and X is selected from the group consisting of:

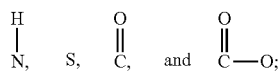

and 2) an enzyme having polyphosphorolysis activity that activates the oligonucleotide P* by removal of the hybridized terminal nucleotide, and (c) polymerizing a nucleic acid by extending the activated oligonucleotide P* on the template strand in presence of four nucleoside triphosphates and a nucleic acid polymerase to synthesize the desired nucleic acid strand; and (d) repeating the steps (a)-(c) as necessary to amplify the target nucleic acid.

2. The method of claim 1 wherein the enzyme is a DNA polymerase.

3. The method of claim 2 wherein the enzyme is a thermostable DNA polymerase.

4. The method of claim 3 wherein the thermostable DNA polymerase is selected from the group consisting of thermostable Tfl, Taq, AMPLITAQFS, THERMOSEQUENASE, RQ1, RQY, THERMINATOR I, THERMINATOR II, THERMINATOR III, and THERMINATOR GAMMA.

5. The method of claim 1 wherein the extending and amplification steps are carried out using a polymerase chain reaction.

6. The method of claim 5 wherein the polymerase chain reaction is a digital polymerase chain reaction.

7. The method of claim 1 using one or more polyphosphorolyzing agents of Formula I:

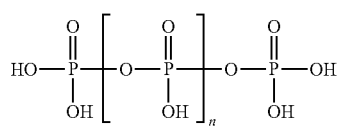

(I)

wherein n is selected from the group consisting of 1, 2, 3, 4, 5, 6, 7, 8, 9, and 10.

8. The method of claim 1 using one or more polyphosphorolyzing agents of Formula II:

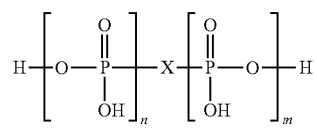

(II)

where n and/or m are selected from the group consisting of 0, 1, 2, 3, 4, 5, 6, 7, 8, 9, and 10, with the proviso that n and m cannot both be 0, and X is selected from the group consisting of:

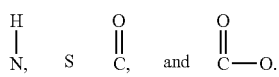

9. The method of claim 1 using one or more polyphosphorolyzing agents selected from the group consisting of:

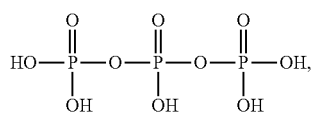

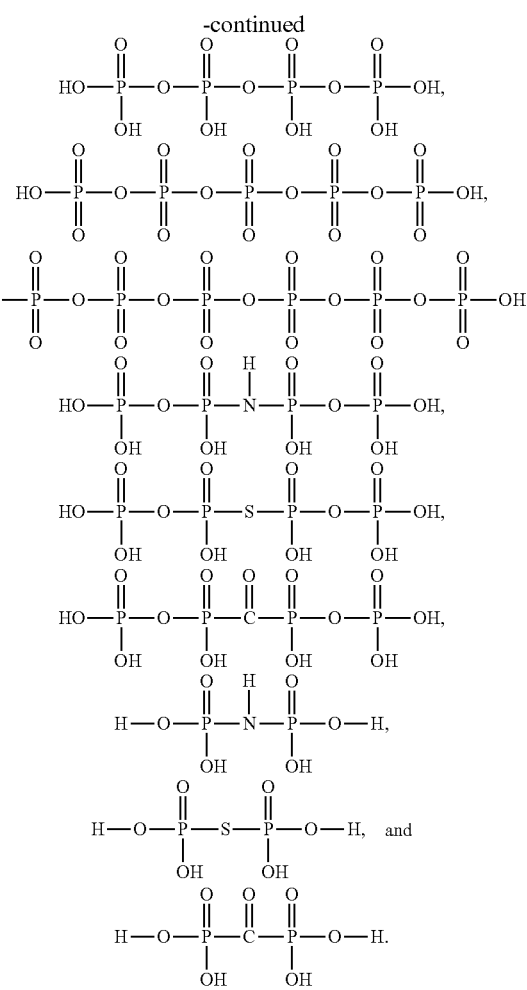

10. The method of claim 9 using one or more polyphosphorolyzing agents selected from the group consisting of triphosphate, tetraphosphate, and imidodiphosphate.

11. The method of claim 1, wherein the polyphosphorolyzing further comprises using pyrophosphate in combination with the one or more polyphosphorolyzing agents.

12. The method of claim 1, further comprising detecting the polymerized nucleic acid.

13. The method of claim 1, wherein the one or more polyphosphorolyzing agents is present in the amplification reaction at a concentration of approximately 1-500 µM.

14. The method of claim 1, wherein the target nucleic acid is RNA.

15. The method of claim 14 wherein the enzyme or polymerase has reverse transcriptase activity.

16. The method of claim 14 wherein the enzyme is RQ1 or its mutant RQY.

17. The method of claim 14 used in a direct RNA sequencing reaction.

* * * * *